United States Patent
Zhang et al.

(10) Patent No.: US 10,155,947 B2
(45) Date of Patent: Dec. 18, 2018

(54) METHOD FOR INHIBITING EBOLA VIRUS VIA MIRNA

(71) Applicant: JIANGSU MICROMEDMARK BIOTECH CO., LTD., Taizhou, Jiangsu (CN)

(72) Inventors: Chenyu Zhang, Jiangsu (CN); Hongwei Liang, Jiangsu (CN); Zhen Zhou, Jiangsu (CN); Ke Zeng, Jiangsu (CN); Xi Chen, Jiangsu (CN)

(73) Assignee: JIANGSU MICROMEDMARK BIOTECH CO., LTD., Taizhou, Jiangsu (CN)

( * ) Notice: Subject to any disclaimer, the term of this patent is extended or adjusted under 35 U.S.C. 154(b) by 0 days.

(21) Appl. No.: 15/507,984

(22) PCT Filed: Sep. 1, 2015

(86) PCT No.: PCT/CN2015/088802
§ 371 (c)(1),
(2) Date: Mar. 1, 2017

(87) PCT Pub. No.: WO2016/034110
PCT Pub. Date: Mar. 10, 2016

(65) Prior Publication Data
US 2017/0240898 A1    Aug. 24, 2017

(30) Foreign Application Priority Data
Sep. 1, 2014   (CN) .......................... 2014 1 0440455

(51) Int. Cl.
| | | |
|---|---|---|
| *C12N 15/113* | (2010.01) | |
| *A61K 48/00* | (2006.01) | |
| *A61K 36/76* | (2006.01) | |
| *A61K 36/81* | (2006.01) | |
| *A61K 36/185* | (2006.01) | |
| *A61K 36/195* | (2006.01) | |
| *A61K 36/31* | (2006.01) | |
| *A61K 36/355* | (2006.01) | |
| *A61K 36/48* | (2006.01) | |

(52) U.S. Cl.
CPC ........ *C12N 15/1131* (2013.01); *A61K 36/185* (2013.01); *A61K 36/195* (2013.01); *A61K 36/31* (2013.01); *A61K 36/355* (2013.01); *A61K 36/48* (2013.01); *A61K 36/76* (2013.01); *A61K 36/81* (2013.01); *A61K 48/00* (2013.01); *C12N 15/113* (2013.01); *C12N 2310/141* (2013.01); *C12N 2330/10* (2013.01)

(58) Field of Classification Search
CPC combination set(s) only.
See application file for complete search history.

(56) References Cited

U.S. PATENT DOCUMENTS 9,752,148 B2 * 9/2017 Zhang ................ C12N 15/1131

FOREIGN PATENT DOCUMENTS

| | | |
|---|---|---|
| CN | 102416185 | 4/2012 |
| CN | 103589721 | 2/2014 |
| WO | WO2014026333 A1 * | 2/2014 |

OTHER PUBLICATIONS

English Translation of WO 2014026333, provided by google on Dec. 13, 2017. pp 1-8 (Year: 2017).*
EurekaAlert! Science News retrieved on Dec. 19, 2017, pp. 1-3 Virological penicillin: Plant MIR2911 directly targets influenza A viruses public release date Oct. 6, 2014 (Year: 2014).*
Zhou et al. Cell Research 2015 25:39-49, published online Oct. 7, 2014 (Year: 2014).*
Neha Karl EurekaAlert! Science News retrieved on Dec. 21, 2017, Honeysuckle Tea can treat influenza a Viruses, and possible Ebola pp. 1-3 public release date Oct. 16, 2014 (Year: 2014).*
Bente et al. Disease Models & Mechanisms 2, 12-17 (Year: 2009).*
International Search Report for international application No. PCT/CN2015/088802, dated Dec. 1, 2015 (8 pages, including English translation).
L. Zhang et al., "Exogenous plant MIR168a specifically targets mammalian LDLRAP1: evidence of cross-kingdom regulation by microRNA," Cell Research, (2012) vol. 22, p. 107-126.
Correction to L. Zhang et al., "Exogenous plant MIR168a specifically targets mammalian LDLRAP1: evidence of cross-kingdom regulation by microRNA," originally published as Cell Research, (2012) vol. 22, p. 107-126, corrected in Cell Research, (2012) vol. 22, p. 273-274.

* cited by examiner

*Primary Examiner* — Brian A Whiteman
(74) *Attorney, Agent, or Firm* — Hamre, Schumann, Mueller & Larson, P.C.

(57) ABSTRACT

Provided are a method and use of microRNA MiR-2911 in regulating an ebola virus. Particularly provided are a method and use of isolated microRNA MiR-2911 in regulating an ebola virus protein gene.

8 Claims, 9 Drawing Sheets
Specification includes a Sequence Listing.

Ebola virus, GP

```
5'UTR                              CDS                                3'UTR
         ┌────────────────────────────┬────────────────────────────┐
─────────┤                            │                            ├─────────
         └────────────────────────────┴────────────────────────────┘
SEQ ID NO.:5                    Binding site 1
Binding site 1   mfe: ΔG=-35.4kcal/mol GP      5'   A       G GAAGC           3'
                                CCA CC  G    UCCCCCGGCC
                                GGU GG  C    AGGGGGCCGG
SEQ ID NO.:1          MIR2911  3'  AG   C  G           seed sequence 5'   SEQ ID NO.:1
```

Figure 1

Ebola virus, VP40

```
5'UTR                              CDS                                3'UTR
         ┌─────────────────────────────────────────────────┐
─────────┤                                                 ├─────────────────
         └─────────────────────────────────────────────────┘
SEQ ID NO.:6                                         SEQ ID NO.:7  Binding site 1  Binding site 2
Binding site 1   mfe: ΔG=-37.2kcal/mol                              Binding site 2   mfe: ΔG=-24.0kcal/mol VP40    5'  A    U   AC             A 3'               VP40    5'  A   A  AA              A 3'
              UUCC GCC    UCCCCGGCC                                  CA UC     CCCCGGC
              AGGG CGG    GGGGGCCGG                                  GU GG     GGGGCCG
MIR2911 3'         U  GCA        seed sequence 5'      MIR2911 3' AGG   C  GCAG      seed sequence G 5'
SEQ ID NO.:1                                           SEQ ID NO.:1
```

Figure 2

SEQUENCE LISTING

```
<160> NUMBER OF SEQ ID NOS: 20

<210> SEQ ID NO 1
<211> LENGTH: 20
<212> TYPE: RNA
<213> ORGANISM: Lonicera japonica

<400> SEQUENCE: 1
ggccggggga cgggcuggga                                          20

<210> SEQ ID NO 2
<211> LENGTH: 20
<212> TYPE: RNA
```

```
<213> ORGANISM: Lonicera japonica

<400> SEQUENCE: 2
ugacagaaga gagugagcac                                                   20

<210> SEQ ID NO 3
<211> LENGTH: 21
<212> TYPE: RNA
<213> ORGANISM: Lonicera japonica

<400> SEQUENCE: 3
ucgcuuggug caggucggga a                                                 21

<210> SEQ ID NO 4
<211> LENGTH: 22
<212> TYPE: RNA
<213> ORGANISM: Lonicera japonica

<400> SEQUENCE: 4
uggaggcagc gguucaucga uc                                                22

<210> SEQ ID NO 5
<211> LENGTH: 36
<212> TYPE: DNA
<213> ORGANISM: Ebola virus

<400> SEQUENCE: 5
ggtaccacca ccgggaagct cccccggccc aagctt                                 36

<210> SEQ ID NO 6
<211> LENGTH: 33
<212> TYPE: DNA
<213> ORGANISM: Ebola virus

<400> SEQUENCE: 6
ggtaccattc ctgccactcc ccggccaaag ctt                                    33

<210> SEQ ID NO 7
<211> LENGTH: 28
<212> TYPE: DNA
<213> ORGANISM: Ebola virus

<400> SEQUENCE: 7
ggtaccacaa tcaaccccgg caaagctt                                          28

<210> SEQ ID NO 8
<211> LENGTH: 4818
<212> TYPE: DNA
<213> ORGANISM: artificial sequence
<220> FEATURE:
<223> OTHER INFORMATION: pGL3-Basic

<400> SEQUENCE: 8
ggtaccgagc tcttacgcgt gctagcccgg gctcgagatc tgcgatctaa gtaagcttgg       60
cattccggta ctgttggtaa agccaccatg gaagacgcca aaaacataaa gaaaggcccg      120
gcgccattct atccgctgga agatggaacc gctggagagc aactgcataa ggctatgaag      180
agatacgccc tggttcctgg aacaattgct tttacagatg cacatatcga ggtggacatc      240
acttacgctg agtacttcga aatgtccgtt cggttggcag aagctatgaa acgatatggg      300
ctgaatacaa atcacagaat cgtcgtatgc agtgaaaact ctcttcaatt ctttatgccg      360
gtgttgggcg cgttatttat cggagttgca gttgcgcccg cgaacgacat ttataatgaa      420
```

```
cgtgaattgc tcaacagtat gggcatttcg cagcctaccg tggtgttcgt ttccaaaaag      480
gggttgcaaa aaattttgaa cgtgcaaaaa aagctcccaa tcatccaaaa aattattatc      540
atggattcta aaacggatta ccagggattt cagtcgatgt acacgttcgt cacatctcat      600
ctacctcccg gttttaatga atacgatttt gtgccagagt ccttcgatag ggacaagaca      660
attgcactga tcatgaactc ctctggatct actggtctgc taaaggtgt cgctctgcct       720 catagaactg cctgcgtgag attctcgcat gccagagatc ctattttggg caatcaaatc      780
attccggata ctgcgatttt aagtgttgtt ccattccatc acggttttgg aatgtttact      840
acactcggat atttgatatg tggatttcga gtcgtcttaa tgtatagatt tgaagaagag      900
ctgtttctga ggagccttca ggattacaag attcaaagtg cgctgctggt gccaacccta      960
ttctccttct tcgccaaaag cactctgatt gacaaatacg atttatctaa tttacacgaa     1020
attgcttctg gtggcgctcc cctctctaag gaagtcgggg aagcggttgc caagaggttc     1080
catctgccag gtatcaggca aggatatggg ctcactgaga ctacatcagc tattctgatt     1140
acacccgagg gggatgataa accgggcgcg tcggtaaag ttgttccatt ttttgaagcg      1200
aaggttgtgg atctggatac cgggaaaacg ctgggcgtta atcaaagagg cgaactgtgt     1260
gtgagaggtc ctatgattat gtccggttat gtaaacaatc cggaagcgac caacgccttg     1320
attgacaagg atggatggct acattctgga gacatagctt actgggacga agacgaacac     1380
ttcttcatcg ttgaccgcct gaagtctctg attaagtaca aaggctatca ggtggctccc     1440
gctgaattgg aatccatctt gctccaacac cccaacatct cgacgcagg tgtcgcaggt      1500 cttcccgacg atgacgccgg tgaacttccc gccgccgttg ttgttttgga gcacggaaag     1560
acgatgacgg aaaagagat cgtggattac gtcgccagtc aagtaacaac cgcgaaaaag      1620
ttgcgcggag gagttgtgtt tgtggacgaa gtaccgaaag gtcttaccgg aaaactcgac     1680
gcaagaaaaa tcagagagat cctcataaag gccaagaagg gcggaaagat cgccgtgtaa     1740
ttctagagtc ggggcggccg gccgcttcga gcagacatga taagatacat tgatgagttt     1800
ggacaaacca caactagaat gcagtgaaaa aaatgcttta tttgtgaaat ttgtgatgct     1860
attgctttat ttgtaaccat tataagctgc aataaacaag ttaacaacaa caattgcatt     1920
cattttatgt ttcaggttca gggggaggtg tgggaggttt tttaaagcaa gtaaacctc      1980 tacaaatgtg gtaaaatcga taaggatccg tcgaccgatg cccttgagag ccttcaaccc     2040
agtcagctcc ttccggtggg cgcggggcat gactatcgtc gccgcactta tgactgtctt     2100
ctttatcatg caactcgtag gacaggtgcc ggcagcgctc ttccgcttcc tcgctcactg     2160
actcgctgcg ctcggtcgtt cggctgcggc gagcggtatc agctcactca aaggcggtaa     2220
tacggttatc cacagaatca ggggataacg caggaaagaa catgtgagca aaaggccagc     2280
aaaaggccag gaaccgtaaa aaggccgcgt tgctggcgtt tttccatagg ctccgccccc     2340
ctgacgagca tcacaaaaat cgacgctcaa gtcagaggtg cgaaacccg acaggactat      2400 aaagatacca ggcgtttccc cctggaagct ccctcgtgcg ctctcctgtt ccgaccctgc     2460
cgcttaccgg atacctgtcc gcctttctcc cttcgggaag cgtggcgctt tctcatagct     2520
cacgctgtag gtatctcagt tcggtgtagg tcgttcgctc caagctgggc tgtgtgcacg     2580
aaccccccgt tcagcccgac cgctgcgcct tatccggtaa ctatcgtctt gagtccaacc     2640
cggtaagaca cgacttatcg ccactggcag cagccactgg taacaggatt agcagagcga     2700
ggtatgtagg cggtgctaca gagttcttga agtggtggcc taactacggc tacactagaa     2760
```

```
gaacagtatt tggtatctgc gctctgctga agccagttac cttcggaaaa agagttggta    2820
gctcttgatc cggcaaacaa accaccgctg gtagcggtgg ttttttttgtt tgcaagcagc    2880 agattacgcg cagaaaaaaa ggatctcaag aagatccttt gatcttttct acggggtctg    2940
acgctcagtg gaacgaaaac tcacgttaag ggattttggt catgagatta tcaaaaagga    3000
tcttcaccta gatcctttta aattaaaaat gaagttttaa atcaatctaa agtatatatg    3060
agtaaacttg gtctgacagt taccaatgct taatcagtga ggcacctatc tcagcgatct    3120
gtctatttcg ttcatccata gttgcctgac tccccgtcgt gtagataact acgatacggg    3180
agggcttacc atctggcccc agtgctgcaa tgataccgcg agacccacgc tcaccggctc    3240
cagatttatc agcaataaac cagccagccg gaagggccga gcgcagaagt ggtcctgcaa    3300
ctttatccgc ctccatccag tctattaatt gttgccggga agctagagta agtagttcgc    3360
cagttaatag tttgcgcaac gttgttgcca ttgctacagg catcgtggtg tcacgctcgt    3420
cgtttggtat ggcttcattc agctccggtt cccaacgatc aaggcgagtt acatgatccc    3480
ccatgttgtg caaaaaagcg gttagctcct tcggtcctcc gatcgttgtc agaagtaagt    3540
tggccgcagt gttatcactc atggttatgg cagcactgca taattctctt actgtcatgc    3600
catccgtaag atgcttttct gtgactggtg agtactcaac caagtcattc tgagaatagt    3660
gtatgcggcg accgagttgc tcttgcccgg cgtcaatacg ggataatacc gcgccacata    3720
gcagaacttt aaaagtgctc atcattggaa aacgttcttc ggggcgaaaa ctctcaagga    3780
tcttaccgct gttgagatcc agttcgatgt aacccactcg tgcacccaac tgatcttcag    3840
catcttttac tttcaccagc gtttctgggt gagcaaaaac aggaaggcaa aatgccgcaa    3900
aaaagggaat aagggcgaca cggaaatgtt gaatactcat actcttcctt tttcaatatt    3960
attgaagcat ttatcagggt tattgtctca tgagcggata catatttgaa tgtatttaga    4020
aaaataaaca ataggggtt ccgcgcacat ttccccgaaa agtgccacct gacgcgccct    4080
gtagcggcgc attaagcgcg gcgggtgtgg tggttacgcg cagcgtgacc gctacacttg    4140
ccagcgccct agcgcccgct cctttcgctt tcttcccttc ctttctcgcc acgttcgccg    4200
gctttccccg tcaagctcta aatcggggc tccctttagg gttccgattt agtgctttac    4260
ggcacctcga ccccaaaaaa cttgattagg gtgatggttc acgtagtggg ccatcgccct    4320
gatagacggt ttttcgccct tgacgttgg agtccacgtt ctttaatagt ggactcttgt    4380
tccaaactgg aacaacactc aaccctatct cggtctattc ttttgattta agggattt    4440 tgccgatttc ggcctattgg ttaaaaaatg agctgattta acaaaaattt aacgcgaatt    4500
ttaacaaaat attaacgctt acaatttgcc attcgccatt caggctgcgc aactgttggg    4560
aagggcgatc ggtgcgggcc tcttcgctat tacgccagcc caagctacca tgataagtaa    4620
gtaatattaa ggtacgggag gtacttggag cggccgcaat aaaatatctt tattttcatt    4680
acatctgtgt gttggttttt tgtgtgaatc gatagtacta acatacgctc tccatcaaaa    4740
caaaacgaaa caaaacaaac tagcaaaata ggctgtcccc agtgcaagtg caggtgccag    4800
aacatttctc tatcgata                                                  4818
```

<210> SEQ ID NO 9
<211> LENGTH: 4808
<212> TYPE: DNA
<213> ORGANISM: artificial sequence
<220> FEATURE:
<223> OTHER INFORMATION: pGL3-GP(CDS)

<400> SEQUENCE: 9

```
ggtaccggta ccaccaccgg gaagctcccc cggcccaagc ttaagcttgg cattccggta      60
ctgttggtaa agccaccatg gaagacgcca aaaacataaa gaaaggcccg gcgccattct     120
atccgctgga agatggaacc gctggagagc aactgcataa ggctatgaag agatacgccc     180
tggttcctgg aacaattgct tttacagatg cacatatcga ggtggacatc acttacgctg     240
agtacttcga aatgtccgtt cggttggcag aagctatgaa acgatatggg ctgaatacaa     300
atcacagaat cgtcgtatgc agtgaaaact ctcttcaatt ctttatgccg gtgttgggcg     360
cgttatttat cggagttgca gttgcgcccg cgaacgacat ttataatgaa cgtgaattgc     420
tcaacagtat gggcatttcg cagcctaccg tggtgttcgt ttccaaaaag gggttgcaaa     480
aaattttgaa cgtgcaaaaa aagctcccaa tcatccaaaa aattattatc atggattcta     540
aaacggatta ccagggattt cagtcgatgt acacgttcgt cacatctcat ctacctcccg     600
gttttaatga atacgatttt gtgccagagt ccttcgatag ggacaagaca attgcactga     660
tcatgaactc ctctggatct actggtctgc ctaaaggtgt cgctctgcct catagaactg     720
cctgcgtgag attctcgcat gccagagatc ctattttggt caatcaaatc attccggata     780
ctgcgatttt aagtgttgtt ccattccatc acggttttgg aatgtttact acactcggat     840
atttgatatg tggatttcga gtcgtcttaa tgtatagatt tgaagaagag ctgtttctga     900
ggagccttca ggattacaag attcaaagtg cgctgctggt gccaacccta ttctccttct     960
tcgccaaaag cactctgatt gacaaatacg atttatctaa tttacgaa attgcttctg    1020
gtggcgctcc cctctctaag gaagtcgggg aagcggttgc caagaggttc catctgccag    1080
gtatcaggca aggatatggg ctcactgaga ctacatcagc tattctgatt acacccgagg    1140
gggatgataa accgggcgcg gtcggtaaag ttgttccatt ttttgaagcg aaggttgtgg    1200
atctggatac cgggaaaacg ctgggcgtta atcaaagagg cgaactgtgt gtgagaggtc    1260
ctatgattat gtccggttat gtaaacaatc cggaagcgac caacgccttg attgacaagg    1320
atggatggct acattctgga gacatagctt actgggacga agacgaacac ttcttcatcg    1380
ttgaccgcct gaagtctctg attaagtaca aaggctatca ggtggctccc gctgaattgg    1440
aatccatctt gctccaacac cccaacatct tcgacgcagg tgtcgcaggt cttcccgacg    1500
atgacgccgg tgaacttccc gccgccgttg ttgttttgga gcacggaaag acgatgacgg    1560
aaaaagagat cgtggattac gtcgccagtc aagtaacaac cgcgaaaaag ttgcgcggag    1620
gagttgtgtt tgtggacgaa gtaccgaaag gtcttaccgg aaaactcgac gcaagaaaaa    1680
tcagagagat cctcataaag gccaagaagg gcggaaagat cgccgtgtaa ttctagagtc    1740
ggggcggccg gccgcttcga gcagacatga taagatacat tgatgagttt ggacaaacca    1800
caactagaat gcagtgaaaa aaatgcttta tttgtgaaat ttgtgatgct attgctttat    1860
ttgtaaccat tataagctgc aataaacaag ttaacaacaa caattgcatt catttatgt    1920
ttcaggttca ggggaggtg tgggaggttt tttaaagcaa gtaaacctc tacaaatgtg    1980
gtaaaatcga taaggatccg tcgaccgatg cccttgagag ccttcaaccc agtcagctcc    2040
ttccggtggg cgcggggcat gactatcgtc gccgcactta tgactgtctt ctttatcatg    2100
caactcgtag gacaggtgcc ggcagcgctc ttccgcttcc tcgctcactg actcgctgcg    2160
ctcggtcgtt cggctgcggc gagcggtatc agctcactca aaggcggtaa tacggttatc    2220
cacagaatca ggggataacg caggaaagaa catgtgagca aaaggccagc aaaaggccag    2280
gaaccgtaaa aaggccgcgt tgctggcgtt tttccatagg ctccgccccc ctgacgagca    2340
```

```
tcacaaaaat cgacgctcaa gtcagaggtg gcgaaacccg acaggactat aaagatacca    2400 ggcgttccc  cctggaagct ccctcgtgcg ctctcctgtt ccgaccctgc cgcttaccgg    2460
atacctgtcc gcctttctcc cttcgggaag cgtggcgctt tctcatagct cacgctgtag    2520
gtatctcagt tcggtgtagg tcgttcgctc caagctgggc tgtgtgcacg aaccccccgt    2580
tcagcccgac cgctgcgcct tatccggtaa ctatcgtctt gagtccaacc cggtaagaca    2640
cgacttatcg ccactggcag cagccactgg taacaggatt agcagagcga ggtatgtagg    2700
cggtgctaca gagttcttga agtggtggcc taactacggc tacactagaa gaacagtatt    2760
tggtatctgc gctctgctga agccagttac cttcggaaaa agagttggta gctcttgatc    2820
cggcaaacaa accaccgctg gtagcggtgg ttttttgtt tgcaagcagc agattacgcg    2880
cagaaaaaaa ggatctcaag aagatccttt gatcttttct acggggtctg acgctcagtg    2940
gaacgaaaac tcacgttaag ggattttggt catgagatta tcaaaaagga tcttcaccta    3000 gatccttta  aattaaaaat gaagttttaa atcaatctaa agtatatatg agtaaacttg    3060
gtctgacagt taccaatgct taatcagtga ggcacctatc tcagcgatct gtctatttcg    3120
ttcatccata gttgcctgac tccccgtcgt gtagataact acgatacggg agggcttacc    3180
atctggcccc agtgctgcaa tgataccgcg agacccacgc tcaccggctc cagatttatc    3240
agcaataaac cagccagccg gaagggccga gcgcagaagt ggtcctgcaa ctttatccgc    3300
ctccatccag tctattaatt gttgccggga agctagagta agtagttcgc cagttaatag    3360
tttgcgcaac gttgttgcca ttgctacagg catcgtggtg tcacgctcgt cgtttggtat    3420
ggcttcattc agctccggtt cccaacgatc aaggcgagtt acatgatccc ccatgttgtg    3480 caaaaagcg  gttagctcct tcggtcctcc gatcgttgtc agaagtaagt tggccgcagt    3540
gttatcactc atggttatgg cagcactgca taattctctt actgtcatgc catccgtaag    3600
atgcttttct gtgactggtg agtactcaac caagtcattc tgagaatagt gtatgcggcg    3660
accgagttgc tcttgcccgg cgtcaatacg ggataatacc gcgccacata gcagaacttt    3720
aaaagtgctc atcattggaa aacgttcttc ggggcgaaaa ctctcaagga tcttaccgct    3780
gttgagatcc agttcgatgt aacccactcg tgcacccaac tgatcttcag catctttac    3840 tttcaccagc gtttctgggt gagcaaaaac aggaaggcaa atgccgcaa aaaagggaat    3900 aagggcgaca cggaaatgtt gaatactcat actcttcctt tttcaatatt attgaagcat    3960
ttatcagggt tattgtctca tgagcggata catatttgaa tgtatttaga aaaataaaca    4020 aatagggtt  ccgcgcacat ttccccgaaa agtgccacct gacgcgccct gtagcggcgc    4080
attaagcgcg gcgggtgtgg tggttacgcg cagcgtgacc gctacacttg ccagcgccct    4140
agcgcccgct cctttcgctt tcttcccttc ctttctcgcc acgttcgccg gctttccccg    4200
tcaagctcta aatcggggc  tccctttagg gttccgattt agtgctttac ggcacctcga    4260
ccccaaaaaa cttgattagg gtgatggttc acgtagtggg ccatcgccct gatagacggt    4320
ttttcgccct ttgacgttgg agtccacgtt ctttaatagt ggactcttgt tccaaactgg    4380
aacaacactc aaccctatct cggtctattc ttttgattta agggattt  tgccgatttc    4440 ggcctattgg ttaaaaatg  agctgattta acaaaaattt aacgcgaatt ttaacaaaat    4500
attaacgctt acaatttgcc attcgccatt caggctgcgc aactgttggg aagggcgatc    4560
ggtgcgggcc tcttcgctat tacgccagcc caagctacca tgataagtaa gtaatattaa    4620
ggtacgggag gtacttggag cggccgcaat aaaatatctt tattttcatt acatctgtgt    4680
gttggttttt tgtgtgaatc gatagtacta acatacgctc tccatcaaaa caaaacgaaa    4740
```
caaaacaaac tagcaaaata ggctgtcccc agtgcaagtg caggtgccag aacatttctc    4800
tatcgata                                                              4808

<210> SEQ ID NO 10
<211> LENGTH: 4800
<212> TYPE: DNA
<213> ORGANISM: artificial sequence
<220> FEATURE:
<223> OTHER INFORMATION: pGL3-VP40(3'UTR)

<400> SEQUENCE: 10
ggtaccggta ccacaatcaa ccccggcaaa gcttaagctt ggcattccgg tactgttggt      60
aaagccacca tggaagacgc caaaaacata agaaaggcc cggcgccatt ctatccgctg     120
gaagatggaa ccgctggaga gcaactgcat aaggctatga agagatacgc cctggttcct     180
ggaacaattg cttttacaga tgcacatatc gaggtggaca tcacttacgc tgagtacttc     240
gaaatgtccg ttcggttggc agaagctatg aaacgatatg gctgaatac aaatcacaga     300 atcgtcgtat gcagtgaaaa ctctcttcaa ttctttatgc cggtgttggg cgcgttattt     360
atcggagttg cagttgcgcc cgcgaacgac atttataatg aacgtgaatt gctcaacagt     420
atgggcattt cgcagcctac cgtggtgttc gtttccaaaa aggggttgca aaaattttg     480 aacgtgcaaa aaagctccc aatcatccaa aaaattatta tcatggattc taaaacggat     540
taccagggat ttcagtcgat gtacacgttc gtcacatctc atctacctcc cggttttaat     600
gaatacgatt ttgtgccaga gtccttcgat agggacaaga caattgcact gatcatgaac     660
tcctctggat ctactggtct gcctaaaggt gtcgctctgc tcatagaac tgcctgcgtg     720 agattctcgc atgccagaga tcctattttt ggcaatcaaa tcattccgga tactgcgatt     780
ttaagtgttg ttccattcca tcacggtttt ggaatgttta ctacactcgg atatttgata     840
tgtggatttc gagtcgtctt aatgtataga tttgaagaag agctgtttct gaggagcctt     900
caggattaca agattcaaag tgcgctgctg gtgccaaccc tattctcctt cttcgccaaa     960
agcactctga ttgacaaata cgatttatct aatttacacg aaattgcttc tggtggcgct    1020
cccctctcta aggaagtcgg ggaagcggtt gccaagaggt tccatctgcc aggtatcagg    1080
caaggatatg gctcactga gactacatca gctattctga ttacacccga ggggatgat    1140 aaaccgggcg cggtcggtaa agttgttcca ttttttgaag cgaaggttgt ggatctggat    1200
accgggaaaa cgctgggcgt taatcaaaga ggcgaactgt gtgtgagagg tcctatgatt    1260
atgtccggtt atgtaaacaa tccggaagcg accaacgcct tgattgacaa ggatggatgg    1320
ctacattctg gagacatagc ttactggac gaagacgaac acttcttcat cgttgaccgc    1380
ctgaagtctc tgattaagta caaaggctat caggtggctc ccgctgaatt ggaatccatc    1440
ttgctccaac accccaacat cttcgacgca ggtgtcgcag tcttcccga cgatgacgcc    1500 ggtgaacttc ccgccgccgt tgttgtttg gagcacggaa agacgatgac ggaaaaagag    1560
atcgtggatt acgtcgccag tcaagtaaca accgcgaaaa agttgcgcgg aggagttgtg    1620
tttgtggacg aagtaccgaa aggtcttacc ggaaaactcg acgcaagaaa aatcagagag    1680
atcctcataa aggccaagaa gggcggaaag atcgccgtgt aattctagag tcggggcggc    1740
cggccgcttc gagcagacat gataagatac attgatgagt ttggacaaac cacaactaga    1800
atgcagtgaa aaaaatgctt tatttgtgaa atttgtgatg ctattgcttt atttgtaacc    1860
attataagct gcaataaaca agttaacaac aacaattgca ttcattttat gtttcaggtt    1920

```
caggggggagg tgtgggaggt tttttaaagc aagtaaaacc tctacaaatg tggtaaaatc    1980
gataaggatc cgtcgaccga tgcccttgag agccttcaac ccagtcagct ccttccggtg    2040 ggcgcgggc atgactatcg tcgccgcact tatgactgtc ttctttatca tgcaactcgt     2100
aggacaggtg ccggcagcgc tcttccgctt cctcgctcac tgactcgctg cgctcggtcg    2160
ttcggctgcg gcgagcggta tcagctcact caaaggcggt aatacggtta ccacagaat    2220 caggggataa cgcaggaaag aacatgtgag caaaaggcca gcaaaaggcc aggaaccgta    2280
aaaaggccgc gttgctggcg ttttttccata ggctccgccc cctgacgag catcacaaaa    2340 atcgacgctc aagtcagagg tggcgaaacc cgacaggact ataaagatac caggcgtttc    2400 ccctggaag ctccctcgtg cgctctcctg ttccgaccct gccgcttacc ggatacctgt     2460
ccgcctttct cccttcggga agcgtggcgc tttctcatag ctcacgctgt aggtatctca    2520
gttcggtgta ggtcgttcgc tccaagctgg gctgtgtgca cgaaccccc gttcagcccg     2580 accgctgcgc cttatccggt aactatcgtc ttgagtccaa cccggtaaga cacgacttat    2640
cgccactggc agcagccact ggtaacagga ttagcagagc gaggtatgta ggcggtgcta    2700
cagagttctt gaagtggtgg cctaactacg gctacactag aagaacagta tttggtatct    2760
gcgctctgct gaagccagtt accttcggaa aaagagttgg tagctcttga tccggcaaac    2820
aaaccaccgc tggtagcggt ggtttttttg tttgcaagca gcagattacg cgcagaaaaa    2880
aaggatctca agaagatcct ttgatctttt ctacggggtc tgacgctcag tggaacgaaa    2940
actcacgtta agggattttg gtcatgagat tatcaaaaag gatcttcacc tagatccttt    3000
taaattaaaa atgaagtttt aaatcaatct aaagtatata tgagtaaact tggtctgaca    3060
gttaccaatg cttaatcagt gaggcaccta tctcagcgat ctgtctattt cgttcatcca    3120
tagttgcctg actccccgtc gtgtagataa ctacgatacg ggagggctta ccatctggcc    3180
ccagtgctgc aatgataccg cgagacccac gctcaccggc tccagattta tcagcaataa    3240
accagccagc cggaagggcc gagcgcagaa gtggtcctgc aactttatcc gcctccatcc    3300
agtctattaa ttgttgccgg gaagctagag taagtagttc gccagttaat agtttgcgca    3360
acgttgttgc cattgctaca ggcatcgtgg tgtcacgctc gtcgtttggt atggcttcat    3420
tcagctccgg ttcccaacga tcaaggcgag ttacatgatc ccccatgttg tgcaaaaaag    3480
cggttagctc cttcggtcct ccgatcgttg tcagaagtaa gttggccgca gtgttatcac    3540
tcatggttat ggcagcactg cataattctc ttactgtcat gccatccgta agatgctttt    3600
ctgtgactgg tgagtactca accaagtcat tctgagaata gtgtatgcgg cgaccgagtt    3660
gctcttgccc ggcgtcaata cgggataata ccgcgccaca tagcagaact ttaaaagtgc    3720
tcatcattgg aaaacgttct cggggcgaa aactctcaag gatcttaccg ctgttgagat    3780
ccagttcgat gtaacccact cgtgcaccca actgatcttc agcatctttt actttcacca    3840
gcgtttctgg gtgagcaaaa acaggaaggc aaaatgccgc aaaaaaggga ataagggcga    3900
cacggaaatg ttgaatactc atactcttcc ttttcaata ttattgaagc atttatcagg     3960
gttattgtct catgagcgga tacatatttg aatgtattta gaaaaataaa caaataggg     4020 ttccgcgcac atttccccga aaagtgccac ctgacgcgcc ctgtagcggc gcattaagcg    4080
cggcgggtgt ggtggttacg cgcagcgtga ccgctacact tgccagcgcc ctagcgcccg    4140
ctcctttcgc tttcttccct tcctttctcg ccacgttcgc cggctttccc cgtcaagctc    4200
taaatcgggg gctcccttta gggttccgat ttagtgcttt acggcacctc gaccccaaaa    4260
aacttgatta gggtgatggt tcacgtagtg gccatcgccc tgatagacg gttttttcgcc     4320
```

```
ctttgacgtt ggagtccacg ttctttaata gtggactctt gttccaaact ggaacaacac   4380
tcaaccctat ctcggtctat tcttttgatt tataagggat tttgccgatt tcggcctatt   4440
ggttaaaaaa tgagctgatt taacaaaaat ttaacgcgaa ttttaacaaa atattaacgc   4500
ttacaatttg ccattcgcca ttcaggctgc gcaactgttg ggaagggcga tcggtgcggg   4560
cctcttcgct attacgccag cccaagctac catgataagt aagtaatatt aaggtacggg   4620
aggtacttgg agcggccgca ataaaatatc tttattttca ttacatctgt gtgttggttt   4680
tttgtgtgaa tcgatagtac taacatacgc tctccatcaa aacaaaacga aacaaaacaa   4740
actagcaaaa taggctgtcc ccagtgcaag tgcaggtgcc agaacatttc tctatcgata   4800
```

```

<210> SEQ ID NO 11
<211> LENGTH: 4805
<212> TYPE: DNA
<213> ORGANISM: artificial sequence
<220> FEATURE:
<223> OTHER INFORMATION: pGL3-VP40(CDS)

<400> SEQUENCE: 11

```

```
ggtaccggta ccattcctgc cactccccgg ccaaagctta agcttggcat tccggtactg     60
ttggtaaagc caccatggaa gacgccaaaa acataaagaa aggcccggcg ccattctatc    120
cgctggaaga tggaaccgct ggagagcaac tgcataaggc tatgaagaga tacgccctgg    180
ttcctggaac aattgctttt acagatgcac atatcgaggt ggacatcact tacgctgagt    240
acttcgaaat gtccgttcgg ttggcagaag ctatgaaacg atatgggctg aatacaaatc    300
acagaatcgt cgtatgcagt gaaaactctc ttcaattctt tatgccggtg ttgggcgcgt    360
tatttatcgg agttgcagtt gcgcccgcga acgacattta taatgaacgt gaattgctca    420
acagtatggg catttcgcag cctaccgtgg tgttcgtttc caaaaagggg ttgcaaaaaa    480
ttttgaacgt gcaaaaaaag ctcccaatca tccaaaaaat tattatcatg gattctaaaa    540
cggattacca gggatttcag tcgatgtaca cgttcgtcac atctcatcta cctcccggtt    600
ttaatgaata cgattttgtg ccagagtcct tcgataggga caagacaatt gcactgatca    660
tgaactcctc tggatctact ggtctgccta aaggtgtcgc tctgcctcat agaactgcct    720
gcgtgagatt ctcgcatgcc agagatccta tttttggcaa tcaaatcatt ccggatactg    780
cgattttaag tgttgttcca ttccatcacg gttttggaat gtttactaca ctcggatatt    840
tgatatgtgg atttcgagtc gtcttaatgt atagatttga agaagagctg tttctgagga    900
gccttcagga ttacaagatt caaagtgcgc tgctggtgcc aaccctattc tccttcttcg    960
ccaaaagcac tctgattgac aaatacgatt tatctaattt acacgaaatt gcttctggtg   1020
gcgctcccct ctctaaggaa gtcggggaag cggttgccaa gaggttccat ctgccaggta   1080
tcaggcaagg atatgggctc actgagacta catcagctat tctgattaca cccgaggggg   1140
atgataaacc gggcgcggtc ggtaaagttg ttccattttt tgaagcgaag gttgtggatc   1200
tggataccgg gaaaacgctg ggcgttaatc aaagaggcga actgtgtgtg agaggtccta   1260
tgattatgtc cggttatgta aacaatccgg aagcgaccaa cgccttgatt gacaaggatg   1320
gatggctaca ttctggagac atagcttact gggacgaaga cgaacacttc ttcatcgttg   1380
accgcctgaa gtctctgatt aagtacaaag gctatcaggt ggctcccgct gaattggaat   1440
ccatcttgct ccaacacccc aacatcttcg acgcaggtgt cgcaggtctt cccgacgatg   1500
acgccggtga acttcccgcc gccgttgttg ttttggagca cggaaagacg atgacggaaa   1560
```

```
aagagatcgt ggattacgtc gccagtcaag taacaaccgc gaaaaagttg cgcggaggag    1620
ttgtgtttgt ggacgaagta ccgaaaggtc ttaccggaaa actcgacgca agaaaaatca    1680
gagagatcct cataaaggcc aagaagggcg gaaagatcgc cgtgtaattc tagagtcggg    1740
gcggccggcc gcttcgagca gacatgataa gatacattga tgagtttgga caaaccacaa    1800
ctagaatgca gtgaaaaaaa tgctttattt gtgaaatttg tgatgctatt gctttatttg    1860
taaccattat aagctgcaat aaacaagtta acaacaacaa ttgcattcat tttatgtttc    1920
aggttcaggg ggaggtgtgg gaggttttttt aaagcaagta aaacctctac aaatgtggta    1980
aaatcgataa ggatccgtcg accgatgccc ttgagagcct tcaacccagt cagctccttc    2040
cggtgggcgc ggggcatgac tatcgtcgcc gcacttatga ctgtcttctt tatcatgcaa    2100
ctcgtaggac aggtgccggc agcgctcttc cgcttcctcg ctcactgact cgctgcgctc    2160
ggtcgttcgg ctgcggcgag cggtatcagc tcactcaaag gcggtaatac ggttatccac    2220
agaatcaggg gataacgcag gaaagaacat gtgagcaaaa ggccagcaaa aggccaggaa    2280
ccgtaaaaag gccgcgttgc tggcgttttt ccataggctc cgcccccctg acgagcatca    2340
caaaaatcga cgctcaagtc agaggtggcg aaacccgaca ggactataaa gataccaggc    2400
gtttccccct ggaagctccc tcgtgcgctc tcctgttccg accctgccgc ttaccggata    2460
cctgtccgcc tttctccctt cgggaagcgt ggcgctttct catagctcac gctgtaggta    2520
tctcagttcg gtgtaggtcg ttcgctccaa gctgggctgt gtgcacgaac cccccgttca    2580
gcccgaccgc tgcgccttat ccggtaacta tcgtcttgag tccaacccgg taagacacga    2640
cttatcgcca ctggcagcag ccactggtaa caggattagc agagcgaggt atgtaggcgg    2700
tgctacagag ttcttgaagt ggtggcctaa ctacggctac actagaagaa cagtatttgg    2760
tatctgcgct ctgctgaagc cagttacctt cggaaaaaga gttggtagct cttgatccgg    2820
caaacaaacc accgctggta gcggtggttt ttttgtttgc aagcagcaga ttacgcgcag    2880
aaaaaaagga tctcaagaag atcctttgat cttttctacg gggtctgacg ctcagtggaa    2940
cgaaaactca cgttaaggga ttttggtcat gagattatca aaaaggatct tcacctagat    3000
ccttttaaat taaaaatgaa gttttaaatc aatctaaagt atatatgagt aaacttggtc    3060
tgacagttac caatgcttaa tcagtgaggc acctatctca gcgatctgtc tatttcgttc    3120
atccatagtt gcctgactcc ccgtcgtgta gataactacg atacgggagg gcttaccatc    3180
tggccccagt gctgcaatga taccgcgaga cccacgctca ccggctccag atttatcagc    3240
aataaaccag ccagccggaa gggccgagcg cagaagtggt cctgcaactt tatccgcctc    3300
catccagtct attaattgtt gccgggaagc tagagtaagt agttcgccag ttaatagttt    3360
gcgcaacgtt gttgccattg ctacaggcat cgtggtgtca cgctcgtcgt ttggtatggc    3420
ttcattcagc tccggttccc aacgatcaag gcgagttaca tgatccccca tgttgtgcaa    3480
aaaagcggtt agctccttcg gtcctccgat cgttgtcaga agtaagttgg ccgcagtgtt    3540
atcactcatg gttatggcag cactgcataa ttctcttact gtcatgccat ccgtaagatg    3600
cttttctgtg actggtgagt actcaaccaa gtcattctga gaatagtgta tgcggcgacc    3660
gagttgctct tgcccggcgt caatacggga taataccgcg ccacatagca gaactttaaa    3720
agtgctcatc attggaaaac gttcttcggg gcgaaaactc tcaaggatct taccgctgtt    3780
gagatccagt tcgatgtaac ccactcgtgc acccaactga tcttcagcat cttttacttt    3840
caccagcgtt tctgggtgag caaaaacagg aaggcaaaat gccgcaaaaa agggaataag    3900
ggcgacacgg aaatgttgaa tactcatact cttcctttttt caatattatt gaagcattta    3960
```

-continued

```
tcagggttat tgtctcatga gcggatacat atttgaatgt atttagaaaa ataaacaaat    4020
aggggttccg cgcacatttc cccgaaaagt gccacctgac gcgccctgta gcggcgcatt    4080
aagcgcggcg ggtgtggtgg ttacgcgcag cgtgaccgct acacttgcca gcgccctagc    4140
gcccgctcct ttcgctttct tcccttcctt tctcgccacg ttcgccggct ttccccgtca    4200
agctctaaat cgggggctcc ctttagggtt ccgatttagt gctttacggc acctcgaccc    4260
caaaaaactt gattagggtg atggttcacg tagtgggcca tcgccctgat agacggtttt    4320
tcgccctttg acgttggagt ccacgttctt taatagtgga ctcttgttcc aaactggaac    4380
aacactcaac cctatctcgg tctattcttt tgatttataa gggattttgc cgatttcggc    4440
ctattggtta aaaatgagc tgatttaaca aaaatttaac gcgaatttta acaaaatatt    4500
aacgcttaca atttgccatt cgccattcag gctgcgcaac tgttgggaag ggcgatcggt    4560
gcgggcctct tcgctattac gccagcccaa gctaccatga taagtaagta atattaaggt    4620 acggaggta cttggagcgg ccgcaataaa atatctttat tttcattaca tctgtgtgtt    4680
ggttttttgt gtgaatcgat agtactaaca tacgctctcc atcaaaacaa aacgaaacaa    4740
aacaaactag caaaataggc tgtccccagt gcaagtgcag gtgccagaac atttctctat    4800
cgata                                                               4805
```

```
<210> SEQ ID NO 12
<211> LENGTH: 36
<212> TYPE: DNA
<213> ORGANISM: artificial sequence
<220> FEATURE:
<223> OTHER INFORMATION: oligonucleotides

<400> SEQUENCE: 12
ggtaccacca ccgggaagct cccccggccc aagctt                              36

<210> SEQ ID NO 13
<211> LENGTH: 36
<212> TYPE: DNA
<213> ORGANISM: artificial sequence
<220> FEATURE:
<223> OTHER INFORMATION: oligonucleotides

<400> SEQUENCE: 13
ggtaccacca ccgggaagct cccccggccc aagctt                              36

<210> SEQ ID NO 14
<211> LENGTH: 36
<212> TYPE: DNA
<213> ORGANISM: artificial sequence
<220> FEATURE:
<223> OTHER INFORMATION: oligonucleotides

<400> SEQUENCE: 14
aagcttgggc cggggagct ccccggtggt ggtacc                               36

<210> SEQ ID NO 15
<211> LENGTH: 33
<212> TYPE: DNA
<213> ORGANISM: artificial sequence
<220> FEATURE:
<223> OTHER INFORMATION: oligonucleotides

<400> SEQUENCE: 15
ggtaccattc ctgccactcc ccggccaaag ctt                                 33
```

```
<210> SEQ ID NO 16
<211> LENGTH: 33
<212> TYPE: DNA
<213> ORGANISM: artificial sequence
<220> FEATURE:
<223> OTHER INFORMATION: oligonucleotides

<400> SEQUENCE: 16
ggtaccattc ctgccactcc ccggccaaag ctt                                33

<210> SEQ ID NO 17
<211> LENGTH: 33
<212> TYPE: DNA
<213> ORGANISM: artificial sequence
<220> FEATURE:
<223> OTHER INFORMATION: oligonucleotides

<400> SEQUENCE: 17
aagctttggc cggggagtgg caggaatggt acc                                33

<210> SEQ ID NO 18
<211> LENGTH: 28
<212> TYPE: DNA
<213> ORGANISM: artificial sequence
<220> FEATURE:
<223> OTHER INFORMATION: oligonucleotides

<400> SEQUENCE: 18
ggtaccacaa tcaacccccgg caaagctt                                     28

<210> SEQ ID NO 19
<211> LENGTH: 28
<212> TYPE: DNA
<213> ORGANISM: artificial sequence
<220> FEATURE:
<223> OTHER INFORMATION: oligonucleotides

<400> SEQUENCE: 19
ggtaccacaa tcaacccccgg caaagctt                                     28

<210> SEQ ID NO 20
<211> LENGTH: 28
<212> TYPE: DNA
<213> ORGANISM: artificial sequence
<220> FEATURE:
<223> OTHER INFORMATION: oligonucleotides

<400> SEQUENCE: 20
aagctttgcc ggggttgatt gtggtacc                                      28
```

METHOD FOR INHIBITING EBOLA VIRUS VIA MIRNA

TECHNICAL FIELD

The present invention relates to the fields of bioinformatics and public health. In particular, the present invention relates to a method for inhibiting Ebola virus using the miRNA. The present invention also provides a method for regulating Ebola virus protein gene using microRNA and application thereof.

BACKGROUND ART

Ebola virus disease is a severe acute viral disease; its typical characteristics and physical signs include acute onset, fever, extreme weakness, muscle pain, headache and sore throat, followed by vomiting, diarrhea, rash, impaired kidney and liver function, and in some cases, both internal and external bleeding. Laboratory findings include low white blood cells and platelet counts, and elevated liver enzymes. Blood and secretions of human would be contagious when they contain viruses. Incubation period can persist 2-21 days.

This disease can affect humans and non-human primates (monkey, gorilla and chimpanzee). The virus is transmitted to people from wild animals (possible natural hosts such as fruit bats, etc.) and spreads in the human population through human-to-human transmission. Wherein, said human-to-human transmission includes direct contact (through broken skin or mucous membranes) with the blood, secretions, organs or other body fluids of infected people, and indirect contact with the environment contaminated with these fluids.

According to the report of World Health Organization by April 2014, the fatality rate of EVD can reach up to 90%, and severely ill patients require intensive supportive treatment.

Those at higher risk of infection when epidemic situation occurs are: health workers; family members or others in close contact with infected people; mourners who have direct contact with the bodies of the deceased during burial ceremonies; and hunters who come into contact with dead animals found in the rainforest area and forest, and the like.

So far, Ebola virus disease infections can only be confirmed through laboratory testing. Samples from patients are of extreme biohazard risk; and testing can only be conducted under maximum biological containment condition (level 4 biosafety laboratory). Health care workers and laboratory workers in other world-wide areas also often face great risk when a major epidemic situation outbreaks regionally.

Ebola virus is mainly transmitted via pathways such as the blood, saliva, sweat and secretions of patients. Laboratory tests often show lymphocytopenia, severe thrombocytopenia and elevated transaminases (AST>ALT), and sometimes blood amylase also elevates. For diagnosis, ELISA can be used for detecting specific IgG antibodies (occurrence of IgM antibody indicates infection); ELISA is used to detect antigens in blood, serum or tissue homogenate; IFA is used to detect viral antigens in liver cells via monoclonal antibodies; or viruses are isolated via cell culture or inoculation to guinea pigs. Viruses can be sometimes observed in liver slices using electron microscope. Misjudgment is often caused by using IFA to detect antibodies, especially when conducting serological investigations of past infections.

Up till now there has been little research on Ebola virus, and there is no good method for preventing, detecting and treating this virus in the world-wide range. So far, in terms of therapy, there is no available specific therapeutic method or vaccine which has acquired scientific confirmations for neither humans nor animals.

Currently, there is an urgent need for a set of research system capable of studying and analyzing the pathogenicity and replication mechanisms of Ebola virus from the view of genomics, further understanding the pathogenic causes and mechanisms of Ebola virus, and designing detection methods and therapeutic methods specifically directed to Ebola virus according to the research results.

In terms of detection, diagnosis is mainly made in prior art through detecting the specific IgM and IgG antibodies against Ebola virus, however, the antibodies in the blood of patients can only occur several days after attack, thus the problem of window phase exists; the viruses have begun to replicate during the window phase and the patients are highly contagious while the antibodies are not completely generated yet, therefore, it is very susceptible to cause the problem of false negatives.

In summary, there is an urgent need in this field for developing a drug capable of effectively inhibiting the replication of Ebola virus or treating Ebola virus, and there is still an urgent need for developing a method capable of being used for accurately detecting Ebola virus.

CONTENTS OF THE INVENTION

One of the objects of the present invention is to provide a drug capable of effectively inhibiting the replication of Ebola virus or treating Ebola virus.

Another object of the present invention is a method of regulating Ebola virus protein gene using plant-derived or artificially synthesized microRNAs.

Another object of the present invention is to provide a method and reagent capable of being used for early accurate detection of Ebola virus.

In a first aspect of the present invention, provided is the use of a microRNA MIR2911, which is used for preparing (a) a drug for treating Ebola virus; (b) a drug for regulating the expression of Ebola virus protein gene; and/or (c) a drug for inhibiting the growth of Ebola virus.

In another preferred example, said drug is used for inhibiting the damage or death of endothelial cell caused by GP of Ebola virus.

In another preferred example, said drug is used for inhibiting the replication of Ebola virus.

In another preferred example, said Ebola virus protein is selected from the group comprising: GP and VP40 or a combination thereof.

In another preferred example, said Ebola virus includes Bundibugyo ebolavirus (BDBV), Zaire ebolavirus (EBOV) and Sudan ebolavirus (SUDV).

In another preferred example, said Ebola virus includes Reston ebolavirus (RESTV) and Tai Forest ebolavirus (TAFV).

In another preferred example, said MIR2911 includes artificially synthesized MIR2911, plant MIR2911, MIR2911 precursor and/or mature form; and/or plants, plant parts, or extracts containing MIR2911.

In another preferred example, said plant is selected from the group consisting of *Lonicera japonica, Isatis tinctoria, Isatis indigotica, Baphicacanthus cusia, Populus diversifolia, Vigna unguiculata*, cotton, Chinese cabbage, *Solanum tuberosum* or combinations thereof.

More preferably, said plant is selected from the group comprising *Lonicera japonica, Isatis tinctoria, Isatis indigotica, Baphicacanthus cusia, Populus diversifolia* or combinations thereof.

Most preferably, said plant is *Lonicera japonica*.

In another preferred example, said Ebola virus protein includes GP, VP40 or a combination thereof.

In another preferred example, said inhibition is realized by means of binding to the CDS region of GP protein and the CDS region or 3'UTR region of VP40.

In a second aspect of the present invention, provided is a composition for inhibiting the replication of Ebola virus and/or treating Ebola virus infection, said composition contains (a) a carrier acceptable in pharmaceutics or bromatology; and (b) active ingredients, said active ingredients include miR2911.

In a third aspect of the present invention, provided is a method for in vitro non-therapeutical inhibition of the replication of Ebola virus or the expression of Ebola virus protein gene, said method comprises the step of having miR2911 contact with Ebola virus or cells infected with Ebola virus.

In another preferred example, said cells are endothelial cells.

In another preferred example, said cells are mammalian cells.

In a fourth aspect of the present invention, provided is a method for preventing or treating Ebola virus diseases, said method comprises the following step: administering MIR2911 or an extract or a composition containing MIR2911 to a subject in need thereof.

In another preferred example, a plant extract containing an effective amount of MIR2911 is administered to a subject in need thereof, or said MIR2911 is mixed with a carrier acceptable in pharmaceutics or bromatology to form a composition.

In another preferred example, said plant is medicinal plants, fruit and vegetable plants and ornamental plants.

In another preferred example, said plant is selected from the group consisting of *Lonicera japonica, Isatis tinctoria, Isatis indigotica, Baphicacanthus cusia, Populus diversifolia, Vigna unguiculata*, cotton, Chinese cabbage, *Solanum tuberosum* or combinations thereof.

More preferably, said plant is selected from the group consisting of *Lonicera japonica, Isatis tinctoria, Isatis indigotica, Baphicacanthus cusia, Populus diversifolia* or combinations thereof.

Most preferably, said plant is *Lonicera japonica*.

In another preferred example, said administration mode includes oral, respiratory tract, injection, transdermal, mucosal, or cavity administration;

In another preferred example, said administration mode includes plasmid injection.

In a fifth aspect of the present invention, provided is the use of the microRNA MIR2911 in preparation of an inhibitor for GP protein of Ebola virus, or the use for preparing an inhibitor or a composition, said inhibitor or composition is used for inhibiting the destruction or death of endothelial cells caused by GP protein of Ebola virus.

It should be understood that all of the various technical features described above and the various technical features specifically described hereinafter (such as examples) can be combined with one another within the scope of the present invention, so as to form new or preferred technical solutions. Due to space limitations, this is no longer tired out one by one.

DESCRIPTION OF DRAWINGS

FIG. 1 shows a schematic diagram for regulating GP gene by MIR2911.

FIG. 2 shows a schematic diagram for regulating VP40 gene by MIR2911.

FIG. 3 shows the structural schematic diagram of the partial plasmids of the present invention, in which FIG. 3A is a plasmid map of luciferase; and FIG. 3B is a plasmid map of β-galactosidase reporter plasmid.

FIG. 5 shows the synthetic principle diagram of Oligo DNA. Thereinto, N1 represents the first base, N2 represents the second base, and so on.

PARTICULAR EMBODIMENTS

Figure 3:
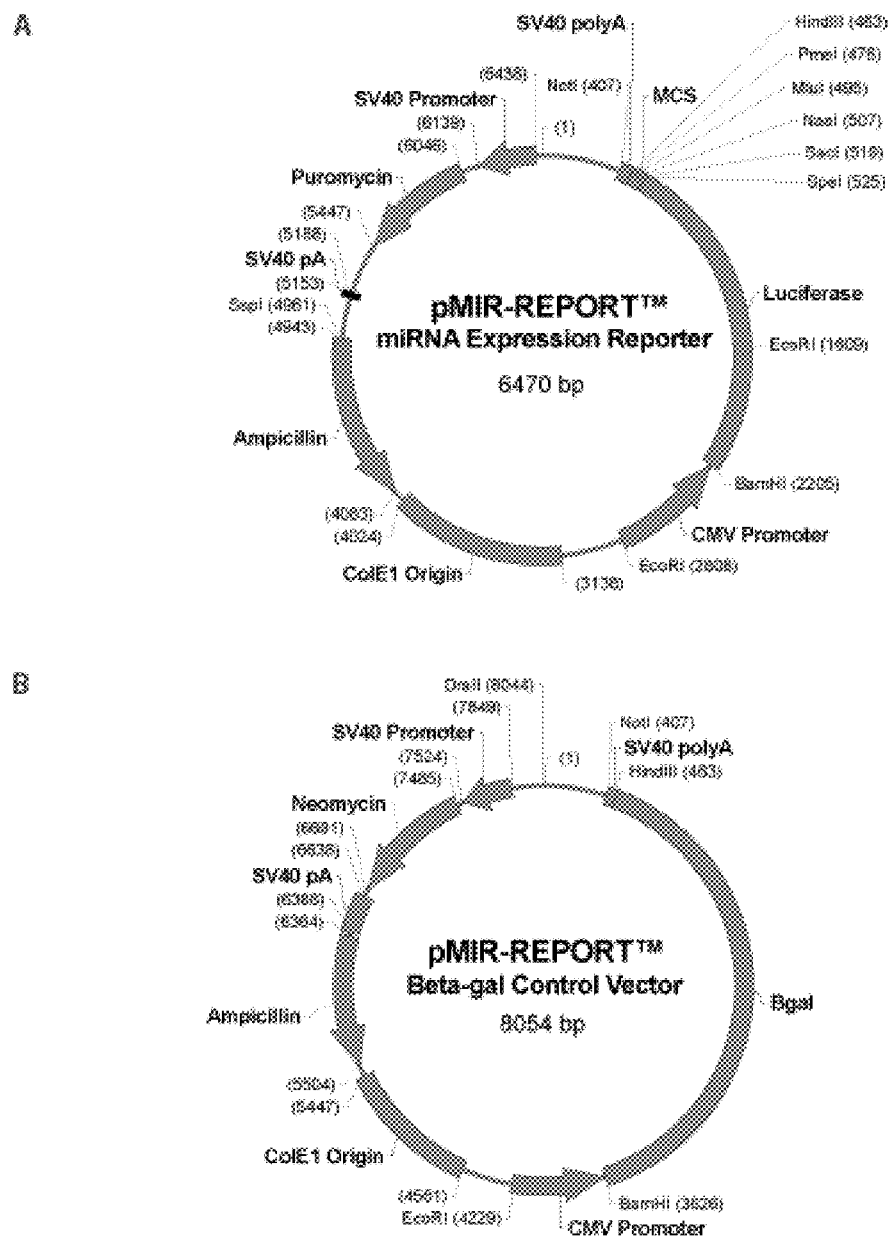

Through conducting broad and deep research and large quantity of screens and experiments, the present inventors become the first to have identified microRNAs capable of effectively binding with genes encoding Ebola virus proteins and inhibiting Ebola virus. In particular, using bioinformatics and luciferase detection method, the present inventors identify a microRNA, i.e., MIR2911, which is capable of binding with the genes of GP protein and VP40 protein of Ebola virus. Experiments demonstrate that microRNA MIR2911 can effectively inhibit the replication of said protein gene of Ebola virus. Further experiments also demonstrate that the methods provided by the present invention have significant inhibiting effects on the pathogenicity of Ebola virus and virus replication, and the present invention is accomplished on this basis.

Based on the above findings, the present inventors provide the following technical solutions:

(a) a method for screening microRNAs that bind with genes encoding Ebola virus proteins.

(b) a method for inhibiting the replication of Ebola virus protein genes;

(c) a microRNA having therapeutic effects on Ebola virus infection and the use thereof in treating Ebola virus infection;

(d) providing the uses of a food and a drug prepared with MIR2911 in treating and/or inhibiting Ebola virus.

In addition, through conducting broad and deep research and genomics analysis on Ebola virus, the present inventors have successfully discovered multiple microRNA precursors and corresponding mature microRNAs of Ebola virus based on the research on three different types of Ebola viruses, and experiments demonstrate that these microRNA precursors in trail can successfully produce sequences of corresponding mature miRNAs. The present inventors have also studied the target genes of these miRNA precursors with designed genomics analysis methods based on these sequences, and indicated the microRNA target genes, which are possibly produced by Ebola virus and their possible influences, providing not only a brand new method for the early diagnosis of Ebola virus infection, but also a possible pathogenic mechanism for Ebola virus infection, as well as a potential target for treating Ebola virus infection.

Terms

Ebola Virus Disease (EVD)

As used herein, "Ebola virus disease", "Ebola virus diseases" and "EVD" can be used exchangeably, the old term "Ebola Hemorrhagic Fever (EBHF)" is a severe infectious disease which is often fatal to humans and primates and mainly occur in remote villages close to tropical rainforest in Central and West Africa.

Ebola Virus

As used herein, "Ebola" and "Ebola virus" and "EBV" can be used exchangeably.

Ebolavirus is one of the three members of Filiviridae (filamentous virus), including 5 different species: Bundibugyo ebolavirus (Bundibugyo virus, BDBV), Zaire ebolavirus (Ebola virus, EBOV), Reston ebolavirus (Reston virus, RESTV), Sudan ebolavirus (Sudan virus, SUDV) and Tai Forest ebolavirus (Tai Forest virus, TAFV). Among them, Bundibugyo ebolavirus, Zaire ebolavirus and Sudan ebolavirus are related to the major epidemic situation of African Ebola virus disease.

Research suggests that Ebola virus is transmitted to human via close contact with blood, secretions, organs or other body fluids of infected animals.

Typical Ebola virus (EBV) belongs to Filoviridae, with the shape of a long filament, being single-stranded negative-strand RNA virus, having 18,959 bases and a molecular weight of $4.17 \times 10^6$. The virus has an envelope outside, the virus particle is about 80 nm in diameter and 100 nm×(300-1500) nm in size, and the virus having relatively strong infecting ability is about 665-805 nm long, being in branch shape, U-shape, 6-shape or circular, while the branch shape is more common, which has an envelope and a 8-10 nm long spike on the surface. Pure virus particle consists of a spiral ribose core-shell composite and contains negative strand linear RNA molecules and 4 virion structural proteins.

Studies show that the replication mechanisms of Ebola virus are as follows: firstly, the RNA-dependent RNA polymerase of the virus binds with the leader sequence of capsid genome, and then the genome is transcribed in sequential order through recognition of the initiation and termination signals of the flanking genome. The mRNA is capped and polyadenylated by L protein during synthesis. The unprocessed primary product transcribed by GP gene during transcription would produce a small molecular non-structural glycoprotein, i.e., sGP, which is highly secreted in infected cells. The subsequent RNA processing process allows the expression of the full-length GP gene.

Figure 6:
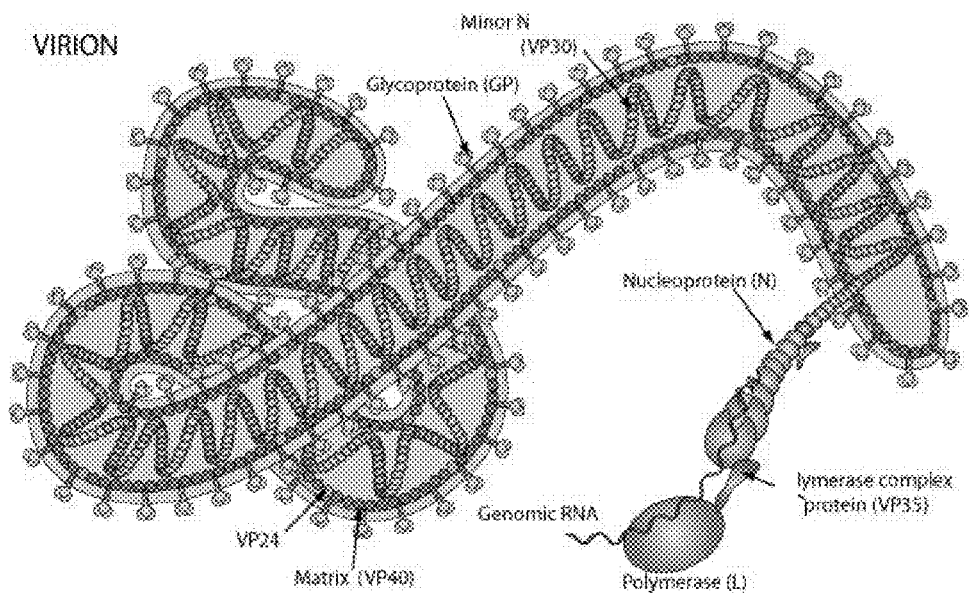
FIG. 6 shows a schematic diagram of filamentous Ebola virus of 970 nm.
Figure 7:
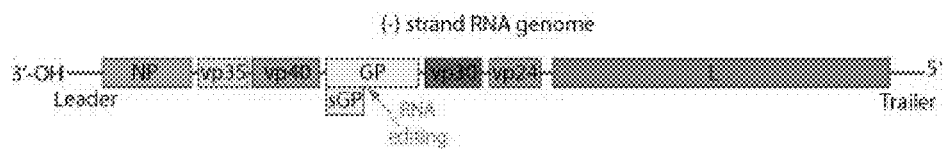
FIG. 7 is a schematic diagram of the genome of Ebola virus.

FIG. 6 shows the schematic diagram of filamentous Ebola virus (about 80 nanometers in diameter), and FIG. 7 shows the linear negative-strand RNA genome of Ebola virus, with a size of 18-19 kb, encoding 7 kinds of proteins.

It is often thought that Ebola virus infection involves the following processes:

(a) adsorption: the viruses firstly attach to host cell receptors through the GP glycoprotein, then enter the cytoplasm of the host cell via microvesicles by means of the endocytosis of the host cell medicated by GP protein;

(b) fusion: the viral outer membrane fuses with microvesicle membrane, and the nucleocapsid is released into the cytoplasm;

(c) subsequent transcription: the virus caps and polyadenylates its mRNA by means of the polymerase in the cytoplasm;

(d) replication: the initiation of replication starts when the nucleoprotein is sufficient for coating the newly-synthesized sense and antisense genomes;

(5) budding: the nucleocapsid contacts with matrix proteins under plasma membrane, and buds via ESCRT complex (Endosomal sorting complex required for transport (ESCRT), ESCRT mainly recognizes ubiquitination-modified membrane proteins and mediates the budding of endocytic vesicles and the formation of multivesicular bodies (MVBs), furthermore, ESCRT also participates in processes such as cytokinesis, autophagy, and budding of enveloped viruses in a similar topology manner) of host plasma membrane.

Currently, the knowledge of Ebola virus partially refers to the following public databases: nucleotide database: NCBI; protein database: UniProtKB.

GP Protein and Gene Thereof

As used in the present invention, "GP protein gene" and "GP gene" can be used exchangeably, which refer to the gene encoding Ebola virus GP protein. Wherein, "GP" refers to Ebola virus glycoprotein.

GP gene can express by means of translation modification and post-expression modification multiple products, which respectively are: secreted glycoprotein (secreted.GP; sGP), glycoprotein (glycoprotein, GP), and small secreted protein (small sGP, ssGP).

sGP is a protein expressed by virus genome and secreted out from cells, and is composed of 364 amino acid residues. Upon expression, modification, and shearing via furin, sGP can compose a 110 kDa homodimer via disulfide bond. So far, the function of sGP is not yet completely clear; it is possibly associated with the virus escaping from host humoral immunity and the repair of endothelial cells. ssGP is another viral nonstructural protein obtained by transcriptional modification of GP gene, which is also referred to as small sGP. Structurally, there are 295 amino acid residues of ssGP which are identical to GP and sGP, however, the role of ssGP during the development of diseases caused by Ebola virus is not yet clear so far.

Ebola virus glycoprotein (GP) is a type I transmembrane glycoprotein encoded by virus GP gene, which is composed of 676 amino acid residues (REBOV type having 677 amino acid residues). Wherein, there are 295 amino acid residues on the amino terminus of GP which are identical to that of sGP, but the difference atcarboxyl terminus decides the enormous difference in GP conformation. Upon expression, GP protein forms two subunits GP1 and GP2 via furin, and GP1 and GP2 form a heterodimer via disulfide bond connected therebetween. Afterwards, GP protein which is composed of GP1 and GP2 subunits forms a tripolymer having a molecular weight of about 450 kDa on the surface of the virus.

Studies show that GP is a crucial component of the envelope of Ebola virus, and plays a crucial role in the invasion of the virus into a host and the exertion of toxic effects.

Mature Ebola virus glycoprotein contains two subunits GP1 and GP2. Wherein, GP1 subunit is crucial to the entry and toxicity of the virus. It contains 469 amino acid residues, and can be divided into three subdomains: a substrate part, a head part and a glycan cap. Wherein, the substrate part of GP1 acts tightly with the GP2 subunit via disulfide bond and stabilizes the conformation of GP2 protein before fusion. The head part of GP1 is located and connected between the substrate part and the glycan cap, and the head part contains a receptor-binding domain related to the virus entry to cells. Furthermore, the glycan cap of the GP1 subunit contains a mucin-like domain associated with the toxicity of GP protein.

GP2 subunit is fixed on the cell membrane by means of a transmembrane segment, which not only stably fixes GP2 subunit, but also is responsible for the fusion of viral cell membrane and the host cell membrane. Although GP2 is a type I transmembrane protein, the fused portion of GP2 is similar to the 13 sheets of type II and type III transmembrane proteins.

GP is not only related to the early phase of viral infection, but also participates in the budding of the virus. Studies show that, during the infection process of Ebola virus, GP preferably binds to endothelial cells, GP firstly anchors Ebola viruses onto target cells via its transmembrane form, then presents the components of the viruses to monocytes and (or) macrophages, which stimulates these cells to release proinflammatory cytokines such as IL21β, TNFα, IL26 and chemokine IL28, pro2α, etc. These cytokines again act on the endothelial cells, destruct the integrity of blood vessels, and result in the symptoms of hemorrhagic fever. GP is expressed in the cells after the endothelial cells are infected by the virus, can induce cell rounding and stripping, and causes cell lesion.

VP40 Protein and Gene Thereof

As used in the present invention, "VP40 protein gene" and "VP40 gene" can be used exchangeably, which refer to the gene encoding Ebola virus VP40 protein.

VP40 is a protein which is most abundant in the virus particles of filamentous viruses, and plays a very important role during the budding of the viruses. VP40 is composed of two domains which are structurally similar and rich in sheetsβ, while these two domains are connected via a "bridge segment" composed of 6 amino acid residues. VP40 can tightly bind with cell membrane via its C-terminus, therefore it has the characteristic of high salt resistance. As compared with other viral proteins, the most prominent characteristic of VP40 lies in that it is capable of generating oligomerization (oligomerization), the full-length EBOV VP40 will generate self-oligomerization after binding with lipid bilayer and expose its N-terminus domain so as to bind with other VP40 monomers. Scientists have isolated the hexamer and octamer of EBOV VP40, and have discovered that their structural elements are VP40 dimer for either VP40 hexamer or octamer. Studies show that EBOV VP40 octamer is a ring-shaped structure, which is composed of four antiparallel dimers, and the dimers form "pocket" shapes at the locations where they are connected with one another, and it can bind with the 5'-U-G-A-3'sequence of RNA, thus making its structure more stable. This kind of VP40 octamer is possibly related to the formation of nucleocapsids of the virus particles, and also possibly participates in the regulation process for the RNA transcription and translation of the virus particles. The structure of VP40 hexamer is similar to that of the octamer, being also ring-shaped structure and also capable of binding with nucleic acid. EBOV VP40 expressed by mammalian cells can be released into culture medium in the form of binding with membrane, in which the C-terminus domain of the VP40 plays an irreplaceable role during the budding of the virus particle. Further studies show that a conservative motif (late domain) of VP40 also plays a very important role during the budding of the virus particles. Late domain mainly has three forms: PTAP, PPXY and YXXL. In addition, late domain can exert the same effect at the different sites of VP40: the releasing activity of the virus-like particles (VLPs) mediated by VP40 would not change when the late domain of the N-terminus of EBOV VP40 is removed and inserted into the C-terminus. Late domain can also interact with cytokines to promote the budding process of the virus. These cytokines include cell proteins such as ubiquitin ligase Need4, Tsg101 and AP-2 protein complex. Wherein, Need4 can bind with PPXY motif, Tsg101 can bind with PTAP motif, and AP-2 protein complex can bind with YXXL motif.

Human Need4 is composed of 4 WW domains rich in proline, while the third WW domain is necessary for binding with VP40. Timmins et al. have found that only the oligomer of VP40 can strongly interact with Nedd4, which indicates that this interaction possibly occurs after the binding of VP40 with cell membrane. VP40 can also bind with Tsg101, which differs from the binding with Nedd4 that Tsg101 can bind with both the monomer and the oligomer of VP40, thus resulting in the increase in the release amount of VLPs. Nedd4 is an ubiquitin ligase capable of regulating the expression of related proteins (such as epithelial sodium channel, EnaC) on the cell surface, and the epithelial sodium channel is capable of making PPXY motif directly act with the WW domain of Nedd4 for recognition. Nedd4 can directly ubiquitinate VP40 and ubiquitinate the host proteins associated with VP40 on the cell surface, which is crucial to the highly efficient release of VLPs. Lipid rafts can function during the process of the assembly and budding of EBOV. The oligomer of VP40 can bind with the microdomains of lipid rafts, while the C-terminus of VP40 plays a crucial role in this kind of binding. Currently, it is believed that the processes for the assembly and budding of EBO V virus particles are as follows: firstly, VP40 monomer binds with multivesicular bodies (MVB) via its C terminus, and this binding makes the conformation of VP40 change and thus VP40 self-oligomerizes. Upon the binding of Nedd4 with the PPXY motif of VP40, VP40 and adjacent proteins can be ubiquitinated. Upon the binding of Tsg101 with ESCRT-1 complex, further in coordination with ESCRT complex n and ESCRT complex 111, they bind with ubiquitinated VP40-MVB complex, and then they altogether are transported to plasma membrane. On the plasma membrane, VP40-MVB complex binds with the tripolymer of a viral protein and gradually form vesicles under the ESCRT complex 111-induced eversion action of membrane, and the ESCRT complex can also promote the gathering of mature virus particles and finally cause the release of the virus particles.

Currently, the studies show that the functions of VP40 mainly include: matrix protein VP40 plays an important role in the assembly and budding of the virus. Firstly, VP40 monomer binds with multivesicular bodies (MVB) via its C terminus, this binding makes the conformation of VP40 change and thus VP40 self-oligomerizes. Upon the binding of Nedd4 with the PPXY motif of VP40, VP40 and adjacent proteins can be ubiquitinated. Upon the binding of Tsg101 with ESCRT-1 complex, further in coordination with ESCRT complex and ESCRT complex, they bind with ubiquitinated VP40-MVB complex, and then they altogether are transported to plasma membrane. On the plasma membrane, VP40-MVB complex binds with the tripolymer of a viral protein and gradually form vesicles under the ESCRT complex-induced eversion action of membrane, and the ESCRT complex can also promote the gathering of mature virus particles and finally cause the release of the virus particles.

MIR2911

As used herein, "microRNA of the present invention", "micro-ribonucleic acid of the present invention", "MIR2911 of the present invention" and "MIR2911" can be used exchangeably, including but not limited to artificially synthesized MIR2911, plant MIR2911, MIR2911 expressed in vivo by plasmids acquired via fermentation method, and various kinds of precursors and/or mature forms of the above-mentioned substances. It should be understood that the term includes (but not limited to): for example pri-MIR2911, pre-MIR2911 and mature MIR2911, etc.

The length of MIR2911 is 20 nt, with the sequence of GGCCGGGGGACGGGCUGGGA (SEQ ID NO.: 1); its GC content is up to 85%, which allows it a broad range of potential action sites.

The naturally derived MIR2911 is one of the numerous plant microRNAs, which is firstly found in *Populus diversifolia*, followed by other plants; its production differs from the traditional processing and maturing processes of plant microRNAs in that it is produced via the expression of plant 26s ribosomal RNA (26s rRNA).

MIR2911 features very high stability. As compared with other plant microRNAs, MIR2911 can still exist in a relatively high content after being steamed and cooked at high temperature and treated with RNAase and the like. Due to its strong stability, it can be widely used in medical products. By means of real-time quantitative PCR detection, MIR2911 is demonstrated to be existing in *Lonicera japonica* in a large amount, with a concentration up to 0.34 pmol/g, which is a potential effective ingredient.

Plant MIR2911 is MIR2911 enriched in the water-soluble and/or liposoluble extracts of said plant.

In another preferred example, said plant includes medicinal plants, fruit and vegetable plants, and ornamental plants; preferably includes *Lonicera japonica, Isatis tinctoria, Isatis indigotica, Baphicacanthus cusia, Populus diversifolia, Vigna unguiculata*, cotton, Chinese cabbage or *Solanum tuberosum*; more preferably, said plant is *Lonicera japonica, Isatis tinctoria, Isatis indigotica, Baphicacanthus cusia* or *Populus diversifolia*; and most preferably, said plant is *Lonicera japonica*.

The administration mode of MIR2911 of the present invention includes, but not limited to: oral, respiratory tract, injection, transdermal, mucosal, or cavity administration.

In another preferred example, the administration mode of MIR2911 includes injection of a plasmid (such as a plasmid expressing MIR2911).

Extraction Method (Preparation Method of Plant Extracts)

The extraction of the plant microRNAs (such as MiR2911) described in the present invention mainly employs the solvent extraction method, that is, a solvent is employed to extract microRNAs from the plants. In this case, said solvent includes water, a hydrophilic solvent, or a combination thereof. Said combination includes adding appropriate amount of a hydrophilic solvent to water or adding appropriate amount of water to a hydrophilic solvent. It should be understood that appropriate amount of auxiliary reagent such as a pH regulator (such as an acid or a base) and the like can also be added to the solvent.

The extraction can be carried out under any appropriate temperature (for example, from normal temperature to the temperature for solvent refluxing); and impregnation method, percolation method, decoction method, refluxing extraction method, continuous extraction method and the like are preferably employed.

During the extraction process, the plants can be pre-treated, for example, the plants are pulverized and subjected to enzyme treatment (such as cellulase, hemicellulase, pectinase, xylanase, neutral protease, papain, glucanase, and complex enzymes) and the like; and also, the extracted mixture can be subjected to post-treatment, for example, a hydrophilic solvent (such as ethanol and the like) can be added to the extracted mixture after extracting the plants with water, which allows the mixture to precipitate via aging.

The obtained liquid after extraction can be used directly and can also be treated via filtration, concentration, and drying (such as freeze drying) to give a solid for subsequent use.

Preferably, the extraction method for the plant microRNAs described in the present invention is a water extraction method.

For instance, the method comprises the steps of taking an appropriate amount of *Lonicera japonica*, pulverizing same, placing *Lonicera japonica* powder in a water bath under a certain temperature (for example, from room temperature to a temperature for refluxing), heating same for several times (such as 1-5 times) with each time incubating for a period of time (such as 0.1-10 hours), and collecting liquid ready for use.

Alternatively, the method comprises the steps of taking an appropriate amount of *Lonicera japonica*, pulverizing same, placing *Lonicera japonica* powder in a water bath under a certain temperature (for example, from room temperature to a temperature for refluxing), heating same for several times (such as 1-5 times) with each time incubating for a period of time (such as 0.1-10 hours), concentrating the extracted liquid to a certain volume, adding an appropriate amount of ethanol to precipitate out a majority of mucilaginous substances, filtrating, and collecting filtrates ready for use.

The plant extracts are collected after extracting the plants, and the varieties and contents of the plant microRNAs in the extracts are determined. The detection method used can be a conventional method in the art, for example (but not limited to): Solexa sequencing technique, real-time PCR, RT-PCR, microarray chip, hybridization in situ, Northern blotting, isothermal rolling circle amplification, microRNA detection based on conjugated polymer and the like.

Compositions

The composition described in the present invention (including a pharmaceutical composition, a food composition or a health care composition) may comprises (a) a carrier acceptable in pharmaceutics or bromatology; and (b) an active ingredient (i.e. the miRNA of the present invention which can inhibit Ebola virus).

Preferably, said composition consists of or substantially consists of components (a) and (b).

In another preferred example, the content of component (b) accounts for 0.01-99 wt % of the total weight of the composition, more preferably 0.1-90 wt % (calculated by microRNA).

The method for preparing said composition comprises the step of mixing the miRNA of the present invention or a plant extract containing the miRNA of the present invention with a carrier acceptable in pharmaceutics or bromatology to form said composition.

The composition is further described, taking a pharmaceutical composition as an example: the pharmaceutical composition of the present invention comprises an active ingredient (such as miR2911) within the scope of a safe and effective amount and a pharmaceutically acceptable excipient or carrier. The "safe and effective amount" herein means that the amount of the active ingredient can obviously relieve pathogenic condition without causing severe side effect. Generally, a pharmaceutical composition contains 1-2000 mg active ingredient/dose, and preferably contains 10-200 mg active ingredient/dose. Alternatively, a pharmaceutical composition contains 0.01-100 micromoles of active ingredient/dose, preferably 0.1-10 micromoles of active ingredient/dose; and more preferably, said "a dose" is an oral solution.

"A carrier acceptable in pharmaceutics" means one or more compatible solid or liquid fillers or gel substances which are suitable for human use and have sufficient purity and low enough toxicity. "Compatibility" herein means that individual components in the composition can be incorporated with the compounds of the present invention and incorporated with one another without obviously reducing the drug effect of the compounds. The examples of the carrier acceptable in pharmaceutics include cellulose and derivatives thereof (such as sodium carboxymethylcellulose, sodium ethyl cellulose, cellulose acetate and the like), gelatin, talc, solid lubricant (such as stearic acid, magnesium stearate), calcium sulfate, a vegetable oil (such as soybean oil, sesame oil, peanut oil, olive oil and the like), polyols (such as propylene glycol, glycerine, mannitol, sorbitol and the like), an emulsifying agent (such as Tween®), a wetting agent (such as sodium lauryl sulfate), a colorant, a flavoring agent, a stabilizing agent, an antioxidant, a preservative, pyrogen-free water and the like.

The administration mode of the composition of the present invention includes oral, respiratory tract, injection, transdermal, mucosal, or cavity administration.

The dosage forms of the composition of the present invention include a tablet, a capsule, a powder, a pill, a granule, a syrup, a solution, a suspension liquid, an emulsion, a suspension, a spray, an aerosol, a powder spray, a volatile liquid, an injection, a powder for injection, a topical solution, a lotion, a pour agent, a liniment, a paste, an eye drop, a nasal drop, an ophthalmic ointment, a mouth wash, a sublingual tablet, or a suppository.

Preferably, the present invention provides the use of a microRNA molecule MIR2911 or an extract containing MIR2911 for preparing a drug to treat Ebola disease. Preferably, said extract (unconcentrated or concentrated) contains 0.01-100 nM (preferably 0.1-20 nM) MIR2911.

microRNAs Specific to Ebola Virus

As used herein, the term "microRNAs specific to Ebola virus" or "the microRNAs of the present invention specific to Ebola virus", "microRNAs encoded by Ebola virus" can be used exchangeably, which refer to 4 kinds of microRNAs derived from Ebola virus, named as EBO-pre-miR-1, EBO-pre-miR-2, EBO-pre-miR-3 and EBO-pre-miR-4. It should be understood that the term includes microRNAs in precursor or mature forms.

The present inventors predict and analyze three different kinds of Ebola viruses by a comprehensive analysis using three kinds of databases and obtain multiple predictive results.

Experiments demonstrate that the three kinds of Ebola viruses can produce 4 kinds of microRNA precursors, while said precursors can produce corresponding mature forms in infected cells, thus function on potential target gene.

The 4 kinds of pre-microRNA precursors provided by the present invention include 1 kind from Reston ebolavirus, 1 kind from Sudan ebolavirus and 2 kinds from Zaire ebolavirus.

Based on the sequence conservativeness analysis on the precursors and mature forms of Ebola virus microRNA, the target genes of the four pre-microRNAs and the possible outcomes of the affect on the target genes are thus judged.

The Main Advantages of the Present Invention Include:

(a) A microRNA which can bind with the GP and VP40 genes encoding Ebola virus proteins is identified for the first time.

2) The microRNA of the present invention can effectively inhibit the replication of GP and/or VP40 protein genes of Ebola virus.

3) The microRNA of the present invention can inhibit the pathogenicity and replication of Ebola virus and be conducive to reduce infection rate.

4) The microRNA of the present invention or the foods and drugs containing said active ingredient have proper effects on treating or ameliorating Ebola virus infection.

5) The microRNA of the present invention has strong targeting efficacy.

The present invention is further illustrated in connection with particular embodiments as follows. It should be understood that these embodiments are merely illustrative of the invention and are not intended to limit the scope of the present invention. In the case of specific conditions for the experimental method being not specified in the following examples, generally conventional conditions are followed, such as the conditions described in Sambrook et al., *Molecular Cloning: A Laboratory Manual* (New York: Cold Spring Harbor Laboratory Press, 1989), or the conditions recommended by the manufacturer. All percentages and parts are weight percentages and weight parts unless otherwise indicated.

Example 1. MIR2911 Decreases the Expression of Genes Encoding Ebola Virus Proteins 1.1 Animal Model Ebola virus is extremely dangerous, the live virus research thereof must be carried out in a level 4 biosafety laboratory, and it is extremely strictly controlled in the world. Pseudotyped virus cannot replicate in vivo and can infect host cells only once, so it can be used as replacement of live virus to study the mechanism of cell entrance and the like. Transgenic mice with genes encoding Ebola virus proteins are constructed using pseudotyped virus.

1.2 Experimental Method

Said transgenic mice with genes encoding Ebola virus proteins are fed with artificially synthesized NC (negative control of microRNA) and various miRNAs such as MIR2911, MiR-156a, MiR-168a, MiR-162a and the like, respectively, and the transgenic mice are induced to express the proteins encoded by Ebola virus.

Afterwards, the expression of the mRNAs of the genes encoding Ebola virus proteins in serum and main organs (liver, spleen, and lung) of the mice is detected using real-time PCR.

Wherein, partial detected miRNA sequences are as follows:

MIR-2911:   GGCCGGGGGACGGGCUGGGA (SEQ ID NO.: 1)

MiR-156a:   UGACAGAAGAGAGUGAGCAC (SEQ ID NO.: 2)

MiR-168a:   UCGCUUGGUGCAGGUCGGGAA (SEQ ID NO.: 3)

MiR-162a:   UGGAGGCAGCGGUUCAUCGAUC (SEQ ID NO.: 4)

The specific operating steps for the detection method using real-time PCR are as follows:

(1) designing primers according to the genes encoding Ebola virus;

(2) extracting the total RNA from the samples, and obtaining cDNA samples by RNA reverse transcription reaction;

(3) adding TaqMan probes or fluorescent dye to perform PCR reaction; and (4) detecting the changes of the amounts of the Ebola virus protein encoding genes in the samples.

As compared with the mice fed with artificially synthesized NC, the expression levels of the genes encoding Ebola virus proteins in serum and main organs (liver, spleen, and lung) of the mice fed with MIR2911 are all significantly decreased, however, for other microRNAs, the expression levels of the genes encoding Ebola virus proteins have not changed.

This indicates that MIR2911 can effectively bind with the genes encoding Ebola virus proteins and effectively inhibit the transcriptions and replications of said protein genes of Ebola virus.

Example 2. MIR2911 Regulates Genes Encoding Ebola Virus Proteins

This example uses bioinformatics and luciferase detection method to validate that MIR2911 regulates GP and VP40 genes encoding Ebola virus proteins.

2.1. MIR2911 Regulates the Gene GP Encoded by Ebola Virus

The schematic diagram for regulation of GP gene by MIR2911 is as shown in FIG. 1. MIR2911 has a binding site with the gene GP encoded by Ebola virus at the CDS region (coding region) (GGTACCACCACCGGGAAGCTC-CCCCGGCCCAAGCTT, SEQ ID NO.: 5) of GP gene, with Gibbs free energy (mfe) reaching −35.4 kcal/mol, mfe represents the minimal folding free energy for the candidate target gene to bind with MIR2911, the greater the absolute value of mfe, the higher the sequence matching degree of the candidate target gene to MIR2911.

The seed sequence of MIR2911 is completely complementary to the binding site of the CDS region of GP gene, the largest loop has only 5 bases, and MIR2911 only has 4 bases which are not complementary to the binding site of the CDS region of GP gene; based on this, MIR2911 can bind with GP gene, and thus it is further validated that MIR2911 can inhibit the expression of GP gene through this binding site.

2.2. MIR2911 Regulates the Gene VP40 Encoded by Ebola Virus

The schematic diagram for regulation of VP40 gene by MIR2911 is as shown in FIG. 2. MIR2911 altogether has two binding sites with the gene VP40 encoded by Ebola virus. The first binding site locates at the CDS region (coding region) (GGTACCATTCCTGCCACTCCCCGGC-CAAAGCTT, SEQ ID NO.: 6) of VP40 gene, with Gibbs free energy (mfe) reaching −37.2 kcal/mol, the seed sequence of MIR2911 is completely complementary to the binding site of the CDS region of VP40 gene, the largest loop has only 3 bases, and MIR2911 only has 4 bases which are not complementary to the binding site of the CDS region of VP40 gene; the second binding site locates at the 3'UTR region (noncoding region) (GGTACCACAATCAAC-CCCGGCAAAGCTT, SEQ ID NO.: 7) of VP40 gene, with Gibbs free energy (mfe) reaching −24.0 kcal/mol, the seed sequence of MIR2911 is completely complementary to the binding site of the 3'UTR region of VP40 gene, the largest loop has only 4 bases, and MIR2911 only has 9 bases which are not complementary to the binding site of the CDS region of VP40 gene. Based on this, MIR2911 can bind with VP40 gene, and thus it is further validated that MIR2911 can inhibit the expression of VP40 gene through this binding site.

2.3. Using Luciferase Detection Method to Validate that MIR2911 Regulates Genes Encoding Ebola Virus Proteins 2.3.1 Basic Information Ebola virus fragments (the binding site extending upstream and downstream 40 bp, respectively) which are predicted through bioinformatics and can be bound with MIR2911 are artificially synthesized, then this product is embedded into the 3'-UTR terminus of a luciferase reporter gene p-MIR-report (Ambion), and pMIR-REPORT miRNA expression reporter gene vector system is used to validate that whether MIR2911 can regulate genes encoded by Ebola virus or not. The plasmid map of the pMIR-REPORT miRNA expression reporter gene vector system is as shown in FIG. 3.

In FIG. 3, the full length of pGL3-Basic vector is 4818 bp (SEQ ID NO.: 8), the information of partial elements thereof are as follows:

TABLE 1

| | |
|---|---|
| promoter | (no) |
| enhancer | (no) |
| multiple cloning region | 1-58 |
| luciferase gene (luc+) | 88-1740 |
| GLprimer2 binding site | 89-111 |
| SV40 late poly(A) signal | 1772-1993 |
| RVprimer4 binding site | 2061-2080 |
| ColE1-derived plasmid replication origin | 2318 |
| beta-lactamase gene (Ampr) | 3080-3940 |
| f1 origin | 4072-4527 |
| Synthetic (upstream) poly(A) signal | 4658-4811 |
| RV primer3 binding site | 4760-4779 |

The sequence of pGL3-GP (CDS) vector is as shown in SEQ ID NO.: 9, wherein the GP (CDS) sequence is located at 7-42 sites.

The sequence of pGL3-VP40 (3'UTR) vector is as shown in SEQ ID NO.: 10, wherein the VP40 (3'UTR) sequence is located at 7-34 sites.

The sequence of pGL3-VP40 (CDS) vector is as shown in SEQ ID NO.: 11, wherein the VP40 (CDS) sequence is located at 7-40 sites.

2.3.2 Construction Process of Vector (a) Design and Synthesis of Oligo DNA

2 Pairs of complementary oligo DNA are designed and synthesized according to known sequences of GP(CDS), VP40(CDS), and VP40(3'UTR), see the corresponding oligo DNA sequences in Table 2:

TABLE 2 oligo DNA sequences

| oligo name | oligo DNA sequence 5'-3' |
| --- | --- |
| GP(CDS): | GGTACCACCACCGGGAAGCTCCCCCGGCCCAAGCTT (SEQ ID NO.: 12) |
| GP(CDS)-U6-1F | GGTACCACCACCGGGAAGCTCCCCCGGCCCAAGCTT (SEQ ID NO.: 13) |
| GP(CDS)-U6-1R | AAGCTTGGGCCGGGGGAGCTTCCCGGTGGTGGTACC (SEQ ID NO.: 14) |
| VP40(CDS): | GGTACCATTCCTGCCACTCCCCGGCCAAAGCTT (SEQ ID NO.: 15) |
| VP40(CDS)-U6-2F | GGTACCATTCCTGCCACTCCCCGGCCAAAGCTT (SEQ ID NO.: 16) |
| VP40(CDS)-U6-2R | AAGCTTTGGCCGGGGAGTGGCAGGAATGGTACC (SEQ ID NO.: 17) |
| VP40(3'UTR): | GGTACCACAATCAACCCCGGCAAAGCTT (SEQ ID NO.: 18) |
| VP40(3'UTR)-U6-1F | GGTACCACAATCAACCCCGGCAAAGCTT (SEQ ID NO.: 19) |
| VP40(3'UTR)-U6-1R | AAGCTTTGCCGGGGTTGATTGTGGTACC (SEQ ID NO.: 20) |

(b) Construction and Validation of Luciferase Plasmid Vector

The synthesized complementary oligo DNAs are dissolved in ddH2O to 100 µM, each complementary single strand is taken 5 µl and mixed pairwise, and annealed according to the system given in Table 2. The oligo mixture is heated at 95° C. for 5 minutes, then placed under room temperature for 20 minutes to form double-stranded DNAs.

The pairwise synthesized oligo DNAs and empty pgl3 plasmids are digested with enzymes KpnI and MluI, the enzyme-digested products after completing the enzyme digestion is recovered using a DNA recovery kit.

The recovered oligo DNAs and empty pgl3 plasmids after enzyme digestion are subjected to ligation reaction at room temperature using T4 DNA ligase.

10 µl ligated product is taken to transform 100 µl competent cells DH5α, followed by spreading on LB plate (containing 50 µg/ml kanamycin) and incubating at 37° C.

3 clones are picked respectively from each plate, followed by shaking same and extracting plasmids, and sequencing to validate whether the inserted fragment sequence in the recombinant clones is consistent with the designed oligo DNA sequence or not.

The pMIR-REPORT miRNA expression reporter gene vector system is composed of an experimental firefly luciferase reporter vector (FIG. 3A) and an associated beta-galactosidase reporter control plasmid (FIG. 3B). By means of inserting predicted miRNA target sequences in the multiple cloning site, pMIR-REPORT Luciferase miRNA Expression Reporter Vector can be used to conduct accurate, quantitative evaluations of miRNA function. pMIR-REPORT luciferase vector contains a firefly luciferase reporter gene under the control of a CMV promoter and terminator. The 3' non-coding region of the luciferase gene contains a multiple cloning site for insertion of binding target sequences of predicted miRNAs or other nucleotide sequences. By means of cloning and inserting predicted miRNA target sequences into pMIR-REPORT vector, the luciferase report expression is subjected to regulation. This mimics the action mode of miRNA target sequence. pMIR-REPORT beta-gal plasmid is a beta-galactosidase reporter plasmid that is designed for normalization exploration for the operating procedures of cell transfection. Beta-galactosidase expressed from this control plasmid can be used to normalize the diversity of expression levels of cells due to the differences in cell viability and transfection efficiency.

The sequencing results show that the plasmid is constructed properly.

When conducting luciferase activity test, firstly the luciferase recombinant plasmid and beta-galactosidase reporter plasmid are co-transfected into 293T cells (beta-galactosidase reporter plasmid is used to determine the transfection efficiency), equal amount of miRNA precursors or artificially synthesized negative control microRNAs are also transfected into 293T cells at the same time, as such, after 24 hours, a luciferase activity test kit (Promega) can be used to detect luciferase activity, and the regulating effect of miRNA on Ebola virus related gene is reflected by the luciferase activity.

Particular Results

Figure 4:
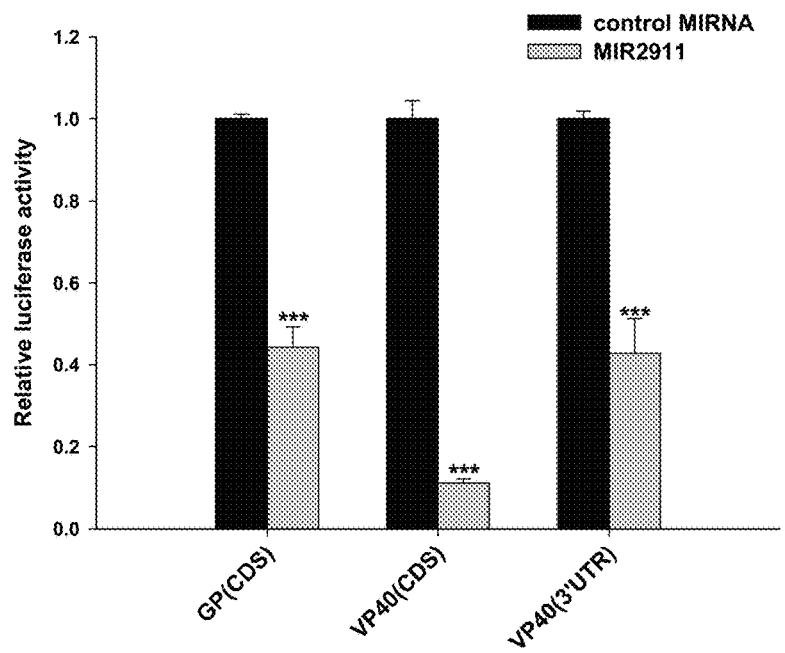
FIG. 4 shows the regulation situation of Ebola virus related gene by MIR2911.

As shown in FIG. 4, MIR2911 can bind with 2 genes of Ebola virus, altogether including 3 sites [GP: its binding site with MIR2911 locates at the CDS region of GP gene, GP(CDS); VP40: it has two binding sites with MIR2911, the first binding site locates at the CDS region of VP40, VP40 (CDS), and the second binding site locates at the 3'UTR region of VP40 gene, VP40(3'UTR)], and all the inhibiting efficiency thereof reach 60%.

It can be seen from FIG. 4 that MIR2911 can bind with the GP and VP40 gene encoded by Ebola virus, can inhibit the invasion and replication of Ebola virus, and thus can be used for treating Ebola virus infection.

Under extremely strict screening condition, MIR2911 still can bind with the two important genes GP and VP40 encoded by Ebola virus, and it is further validated through luciferase experiment that MIR2911 indeed can bind with the genes encoding Ebola virus proteins.

Example 3. Preparation of MIR2911

3.1. Preparation and Extraction Method of Artificially Synthesized MIR2911

Figure 5:
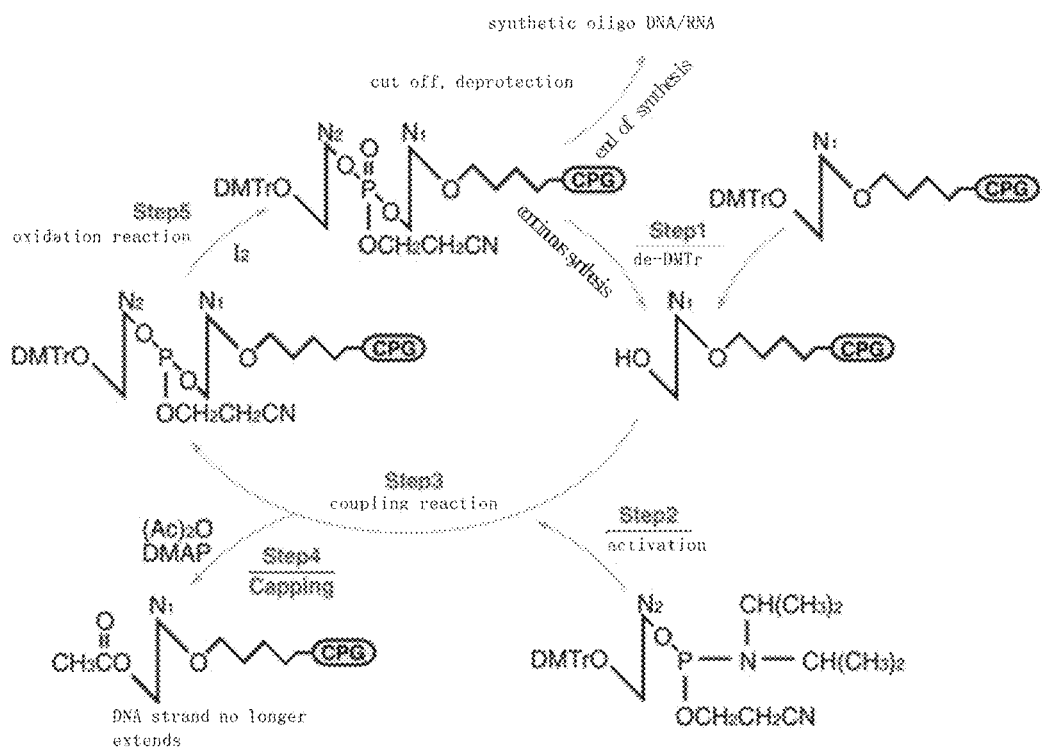

For artificially synthesized MIR2911, oligo DNA/RNA artificial chemical synthesis method is preferably employed, and Oligo DNA/RNA is chemically synthesized using beta-acetonitrile phosphoramidite, the synthesis is performed in the direction from 3' to 5', and generally the first base at the 3' end binds to Glass support (Controlled Pore Glass, CPG). The detailed procedures of synthesis are described in FIG. 5, now stated briefly as follows:

(a). removing the protecting group (DMTr) on the 5'-OH group of the first base attached to CPG support and preparing to attach the next new base;

(b). activating a new base monomer (phosphoramidite) and preparing to react same with the first base;

(c). allowing the coupling reaction of the second base with the first base;

(d). capping 5'-OH of the first base which does not react, so as to stop it from participating in reaction again;

(e). oxidizing nucleoside phosphites into more stable nucleoside phosphate (that is, trivalent phosphorus is oxidized to pentavalent phosphorus).

(f). repeating cycles of 1-5 until the synthesis of the desired Oligo DNA/RNA sequence is completed.

(g). As the synthesis completes, cutting the Oligo DNA/RNA molecule from CPG and further purifying same.

3.2 Other Synthesis Methods of MIR2911

A particular method comprises the following steps:

(a) designing primers for synthesizing MIR2911:

Two universal primers A, B are synthesized according to the template plasmid sequence of MIR2911, and 4 specific oligonucleotide primer sequences (I, II, III, IV) are designed according to the MIR2911 sequence;

(b) first round of PCR amplification:

PCR amplification is performed using a plasmid containing MIR2911 as a template, and A and IV, III and II, I and B as primer combinations, respectively; PCR reaction conditions are: 95° C., 2 minutes for 1 cycle→95° C., 30 seconds, 55° C., 30 seconds, 72° C., 40 seconds for 24 cycles→72° C., 7 minutes; product 1, product 2, and product 3 are obtained, respectively;

(c) second round of PCR amplification: PCR amplification is performed using the product 1, product 2, and product 3 obtained in the first round of PCR amplification as templates, and A and B as primers; PCR reaction conditions are: 95° C., 2 minutes for 1 cycle→95° C., 30 seconds, 55° C., 30 seconds, 72° C., 1 minute 30 seconds for 24 cycles→72° C., 7 minutes, and PCR products are recovered by means of agarose gel to obtain synthesized MIR2911;

(d) methylating the synthesized MIR2911 to form stable methylated product MIR2911.

3.3. Preparation and Extraction Method of Plant MIR2911

A variety of plants including medicinal plants, fruit and vegetable plants, and ornamental plants are rich in MIR2911, such as *Lonicera japonica, Isatis tinctoria, Isatis indigotica, Baphicacanthus cusia, Populus diversifolia, Vigna unguiculata*, cotton, Chinese cabbage or *Solanum tuberosum*.

The extraction method of plant MIR2911 mainly employs a solvent extraction method, that is, a solvent is employed to extract MIR2911 from plants. In this case, said solvent includes water, a hydrophilic solvent, or a combination thereof. Said combination includes adding appropriate amount of a hydrophilic solvent to water or adding appropriate amount of water to a hydrophilic solvent. It should be understood that an appropriate amount of an auxiliary reagent such as a pH regulator (such as an acid or a base) and the like can also be added to the solvent.

The extraction can be carried out under any appropriate temperature (for example, from normal temperature to the temperature for solvent refluxing); and impregnation method, percolation method, decoction method, refluxing extraction method, continuous extraction method and the like are preferably employed.

During the extraction process, the plants can be pretreated, for example, the plants are pulverized and subjected to enzyme treatment (such as cellulase, hemicellulase, pectinase, xylanase, neutral protease, papain, glucanase, and complex enzymes) and the like; and also, the extracted mixture can be subjected to post-treatment, for example, a hydrophilic solvent (such as ethanol and the like) can be added to the extracted mixture after extracting the plants with water, which allows the mixture to precipitate via aging.

The obtained liquid after extraction can be used directly and can also be treated via filtration, concentration, and drying (such as freeze drying) to give a solid for subsequent use.

Preferably, the extraction method for the plant microRNAs described in the present invention is a water extraction method.

Hereinafter, *Lonicera japonica* plant is used as a raw material to prepare and extract MIR2911. However, the plant materials for preparing MIR2911 are not limited to *Lonicera japonica*; said preparation and extraction methods are applicable to medicinal plants, fruit and vegetable plants, and ornamental plants.

*Lonicera japonica* contains a naturally occurred broad spectrum antiviral drug MIR2911.

```
                                        (SEQ ID NO.: 1)
>peu-MIR2911       GGCCGGGGGACGGGCUGGGA
```

*Lonicera japonica* MIR2911 is extracted using water extraction method. An appropriate amount (50 grams) of dried *Lonicera japonica* is taken, followed by heating same in 100° C. water bath with 500 ml water (the ratio of the mass of *Lonicera japonica* to the volume of water is 1:10) for 0.5 hours, and concentrating the extract liquid at 60° C. under reduced pressure to 1/10 of its original volume. The concentrated and unconcentrated *Lonicera japonica* water extracts are collected, and the *Lonicera japonica* MIR2911 is stored for subsequent experiments.

3.4 Expression In Vivo by Plasmids Obtained Via Fermentation Method

MIR2911 precursor is constructed into a plasmid through an artificially designed method, the plasmid is transformed into *Escherichia coli*, fermentation product is recovered via a fermentation method, and the plasmid is extracted and further purified for use in subsequent experiments.

Example 4. MIR2911 has an Inhibiting Effect on Genes Encoding Ebola Virus Proteins The artificially synthesized MIR2911, plant MIR2911, and MIR2911 produced in organisms by plasmids obtained via a fermentation method have an inhibiting effect on Ebola virus through oral, respiratory tract, injection, transdermal, mucosal, or cavity administration.

Ebola virus is extremely dangerous; the live virus research thereof must be carried out in a level 4 biosafety laboratory and is extremely strictly controlled in the world. Pseudotyped virus cannot replicate in vivo and can infect host cells only once, so it can be used as ideal replacement for live virus to study its mechanism of cell entrance and the like. Firstly, transgenic mice are induced to express the genes encoding Ebola virus proteins, then various physiological indexes including the body weight and death rate of the mice are observed; the mice are sacrificed, the expression situation of the mRNAs of protein-encoding genes is detected using real-time PCR; the expression level of GFP detected by western blotting indicates the expression situation of the proteins encoded by Ebola virus; and various items of pathological changes of the main organs (heart, liver, spleen, lung, and kidney), as well as the cardiovascular system and immune system of the mice are observed using frozen section or paraffin section and flow cytometry technique.

Results (a) MIR2911 Ameliorates Symptoms of Infected Mice (a1) Feeding Artificially Synthesized MIR2911 Ameliorates Symptoms of Infected Mice Firstly, transgenic mice are fed with artificially synthesized NC (MIR2911 control) and MIR2911, respectively, then various physiological indexes including the body weight and death rate of the mice are observed; the mice are sacrificed, the expression situation of the mRNAs of the genes encoding Ebola virus proteins is detected using real-time PCR; the expression level of GFP detected by western blotting indicates the expression situation of the proteins encoded by Ebola virus; and various items of pathological changes of the main organs (heart, liver, spleen, lung, and kidney), as well as the cardiovascular system and immune system of the mice are observed using frozen section or paraffin section and flow cytometry technique.

The expression levels of the mRNAs of encoding genes of Ebola virus are detected using real-time PCR, the specific operating procedures are as described in example 1.

The expression levels of the proteins encoded by Ebola virus are detected using conventional Western blotting method. The method comprises the steps of extracting proteins, SDS-PAGE, membrane transfer, immunoreaction, chemoluminescence, gel image analysis, etc.

In the step of gel image analysis, the gel film is scanned or photographed, and the molecular weight and net optical density value of the target band are analyzed using a gel image processing system.

Furthermore, various items of pathological changes of the main organs as well as the cardiovascular system and immune system of the mice are observed using conventional frozen section or paraffin section and flow cytometry technique.

The results show that, as compared with the transgenic mice fed with artificially synthesized NC, the expression levels of the proteins encoded by Ebola virus in the bodies of the transgenic mice fed with artificially synthesized MIR2911 significantly decrease, the main organs (heart, liver, spleen, lung, and kidney) as well as the cardiovascular system and immune system of the mice are ameliorated significantly, and the disease symptoms of the mice are relieved obviously.

The above-mentioned experimental results indicate that feeding with artificially synthesized MIR2911 can inhibit the expression of the proteins encoded by Ebola virus.

(a2) Intravenous Injection of Overexpression Plasmids of MIR2911 Ameliorates Symptoms of Infected Mice Transgenic mice are subjected to tail vein injection of blank control plasmids and overexpression plasmids of MIR2911, respectively, then various physiological indexes including the body weight and death rate of the mice are observed; the mice are sacrificed, the expression situation of the mRNAs of the encoding genes of Ebola virus is detected using real-time PCR; the expression level of GFP detected by western blotting is used to reflect the expression situation of the proteins encoded by Ebola virus; and various items of pathological changes of the main organs (heart, liver, spleen, lung, and kidney) as well as the cardiovascular system and immune system of the mice are observed using frozen section or paraffin section and flow cytometry technique.

The expression levels of the mRNAs of encoding genes of Ebola virus are detected using real-time PCR, the specific operating procedures are as described in example 1.

The expression levels of the proteins encoded by Ebola virus are detected using Western blotting.

Various items of pathological changes of the main organs as well as the cardiovascular system and immune system of the mice are observed using frozen section or paraffin section and flow cytometry technique.

The results show that, as compared with the transgenic mice subjected to tail vein injection of blank control plasmids, the expression levels of the proteins encoded by Ebola virus in the bodies of the transgenic mice subjected to tail vein injection of the overexpression plasmids of MIR2911 decrease significantly, the main organs (heart, liver, spleen, lung, and kidney) as well as the cardiovascular system and immune system of the mice are ameliorated significantly, and the disease symptoms of the mice are relieved obviously.

The above-mentioned experimental results indicate that tail vein injection of the overexpression plasmids of MIR2911 can inhibit the expression of the proteins encoded by Ebola virus.

(a3) Plants Rich in MIR2911 Ameliorate Symptoms of Infected Mice

The transgenic mice are fed with a plant free of MIR2911 (rice) and a plant rich in MIR2911 (*Lonicera japonica*), respectively, various indexes including the body weight and death rate of the mice are observed; the mice are sacrificed, the expression situation of the mRNAs of the genes encoding Ebola virus proteins is detected using real-time PCR; the expression level of GFP detected by western blotting indicates the expression situation of the proteins encoded by Ebola virus; and various items of pathological changes of the main organs (heart, liver, spleen, lung, and kidney) as well as the cardiovascular system and immune system of the mice are observed using frozen section or paraffin section and flow cytometry technique.

The expression levels of the mRNAs of the genes encoding Ebola virus proteins are detected using real-time PCR.

The expression levels of the proteins encoded by Ebola virus are detected using Western blotting.

Various items of pathological changes of the main organs as well as the cardiovascular system and immune system of the mice are observed using frozen section or paraffin section and flow cytometry technique.

The results show that, as compared with the transgenic mice fed with the plant free of MIR2911, the expression levels of the proteins encoded by Ebola virus in the bodies of the transgenic mice fed with the plant rich in MIR2911 decrease significantly, the main organs (heart, liver, spleen, lung, and kidney) as well as the cardiovascular system and immune system of the mice are ameliorated significantly, and the disease symptoms of the mice are relieved obviously.

The experimental results above indicate that feeding with a plant rich in MIR2911 can powerfully inhibit the expressions of the proteins encoded by Ebola virus.

In conclusion, the present invention demonstrates that MIR2911 can inhibit the expressions of the genes encoding Ebola virus proteins in multiple administration modes.

Figure 8:
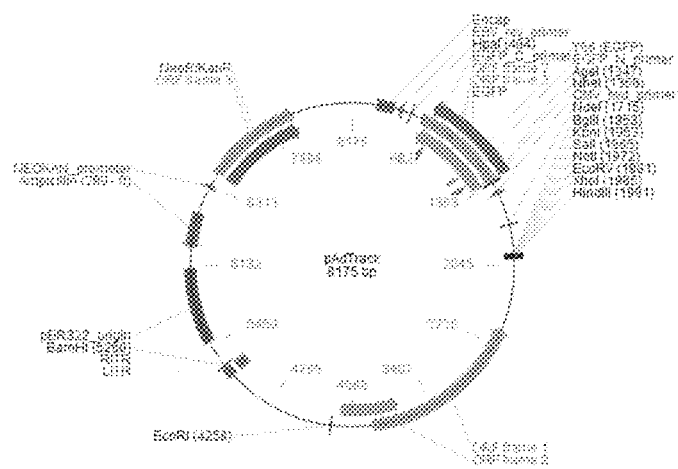
FIG. 8 shows a schematic diagram of adenovirus with GP gene expressed by Ebola virus coupling eGFP.
Figure 9:
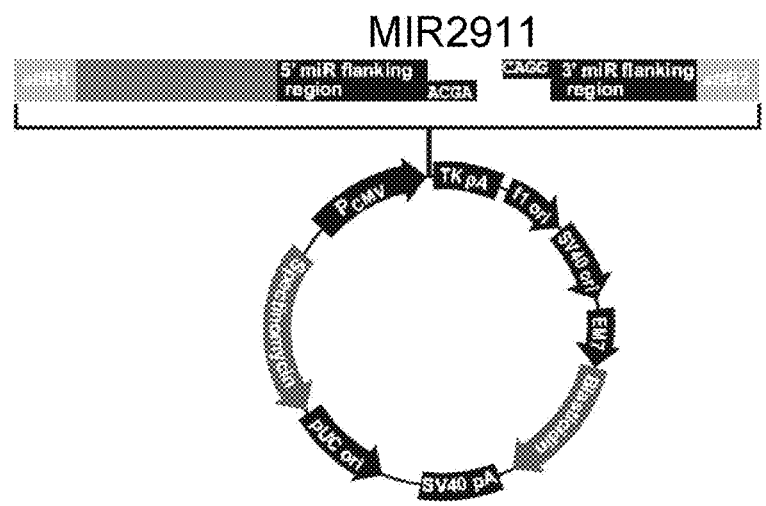
FIG. 9 shows a map of the MIR2911 over-expression plasmid.

Example 5 Validation of the Inhibiting Effect by MIR2911 on the Ebola Encoding GP Gene in HUVEC Cells Common experiment methods are applied to construct adenoviruses that express eGFP coupled, Ebola encoding GP gene (FIG. 8) and MIR2911 over-expression plasmids (FIG. 9).

HUVEC cells are infected with adenoviruses that express eGFP coupled, Ebola encoding GP gene for 12 hours, then the adenovirus infected HUVEC cells are transfected with MIR2911 precursor mimics or MIR2911 over-expression plasmids; 48 hours after the transfection, the expression of green fluorescent proteins is observed with a fluorescent microscope, followed by the collection of RNA and proteins; then the content alteration of GP gene mRNA and protein is detected with q-PCR and western blotting.

Figure 10:
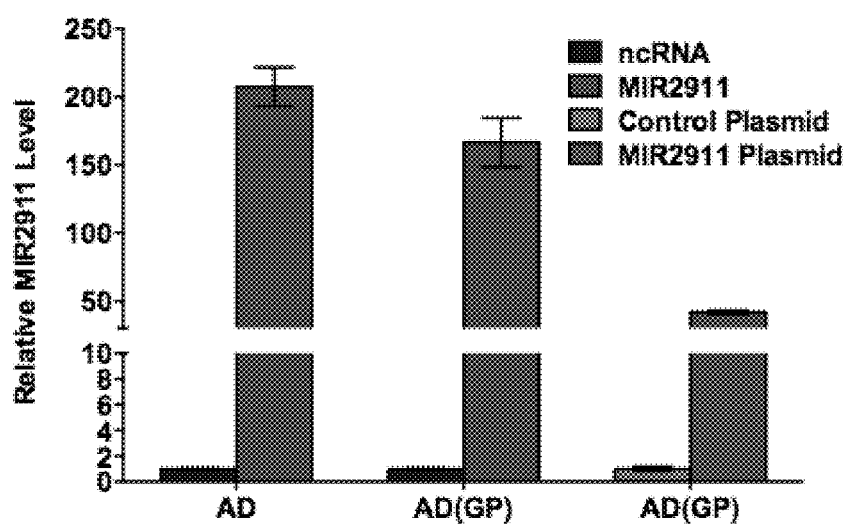
FIG. 10 shows the expression level of MIR2911 in HUVEC cell after being transfected with MIR2911.

The results are shown as follows:

FIG. 10 shows the expression level of MIR2911 in the HUVEC cells after MIR2911 transfection.

Being compared with HUVEC cells transfected with random control nucleoacids or blank pcDNA6.2 plasmids, the MIR2911 level in HUVEC cells transfected with MIR2911 precursor mimics or MIR2911 over-expression plasmids is significantly elevated.

Figure 11:
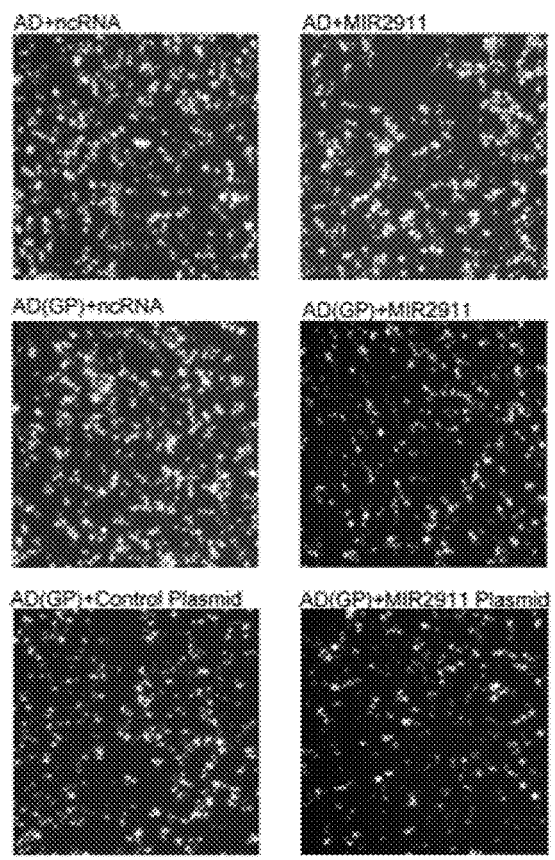
FIG. 11 shows the expression level of eGFP after being transfected with MIR2911.

FIG. 11 shows the expression level of eGFP after MIR2911 transfection.

Being compared with the control groups with 12 hours infection of blank adenovirus, followed by transfection with random control nucleoacids, and that with 12 hours infection of adenoviruses that express eGFP coupled, Ebola encoding GP gene, followed by transfection with blank pcDNA6.2 plasmids, the transfection with MIR2911 precursor mimics or MIR2911 over-expression plasmids can significantly inhibit the expression of green fluorescent protein in the adenoviruses that express eGFP coupled, Ebola encoding GP gene, while forming no effect on the green fluorescent proteins expressed in the blank adenoviruses.

Figure 12:
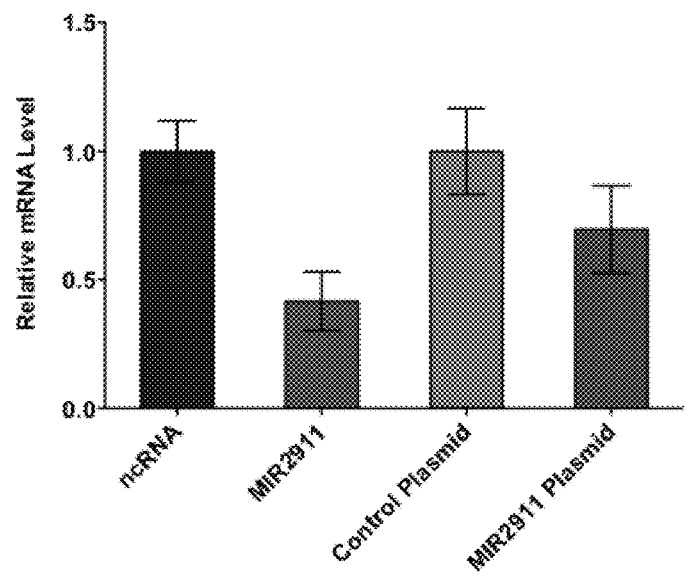
FIG. 12 shows the real-time PCR determination results of GP mRNA.

FIG. 12 shows the detection results of GP mRNA with Q-PCR.

ncRNA:transfection with random control nucleoacids after 12 h infection of adenovirus that expresses eGFP coupled, Ebola encoding GP gene; MIR2911: transfection with MIR2911 precursor mimics after 12 h infection of adenoviruses that express eGFP coupled, Ebola encoding GP gene; Control Plasmid: transfection with blank pcDNA6.2 plasmids after 12 h infection of adenoviruses that express eGFP coupled, Ebola encoding GP gene; MIR2911 Plasmid: transfection with MIR2911 over-expression pcDNA6.2 plasmids after 12 h infection of adenovirus that expresses eGFP coupled, Ebola encoding GP gene.

The GP mRNA level is detected with Q-PCR, and the detection result shows that:

Being compared with the ncRNA and Control Plasmid group, the GP mRNA in the group of MIR2911 precursor mimics transfection (MIR2911), and of MIR2911 over-expression plasmids transfection, is significantly reduced.

Figure 13:
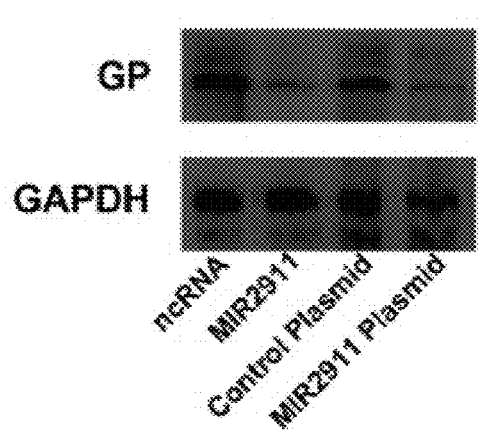
FIG. 13 shows the results of western blotting for the protein level of GP.

FIG. 13 shows the western blotting results of GP protein level.

ncRNA:transfection with random control nucleoacids after 12 h infection of adenovirus that expresses eGFP coupled, Ebola encoding GP gene; MIR2911: transfection with MIR2911 precursor mimics after 12 h infection of adenoviruses that express eGFP coupled, Ebola encoding GP gene; Control Plasmid: transfection with blank pcDNA6.2 plasmids after 12 h infection of adenoviruses that express eGFP coupled, Ebola encoding GP gene; MIR2911 Plasmid: transfection with MIR2911 over-expression pcDNA6.2 plasmids after 12 h infection of adenovirus that expresses eGFP coupled, Ebola encoding GP gene.

Being compared with the ncRNA and Control Plasmid group, the GP protein level in the group of MIR2911 precursor mimics transfection, or of MIR2911 over-expression plasmids transfection, is also significantly reduced.

Example 11. Validation of the Effect of MIR2911 on the Death of Endothelial Cells Induced by GP Gene Encoded by the Ebola Virus in HUVEC Cells GP protein can induce a large number of endothelial cells into non-programmed cell death, which harms to the integrity of Ebola virus patients' blood vessels, causing a series of symptoms such as internal bleeding. In order to observe the effect of GP on cell state, the cell death of HUVEC cell affected by GP is observed using Trypan blue staining at 12 h, 24 h and 36 h. Meanwhile, the effect of GP protein on the integrity of endothelial cell membrane is detected with the CytoTox-Glo™ cytotoxicity assay kit (Purchased from Promega).

Operation steps of Trypan blue staining are as follows:

1. 4% the mother liquid of trypan blue: weigh 4 g trypan blue, grind with a small amount of distilled water, and add distilled water to 100 ml, filter using filter paper, and then to store at 4 degrees centigrade. Upon application, the solution is further diluted with PBS to 0.4%.

2. Single cell suspension is prepared from adherent cells digested with trypsin enzyme, and then appropriate dilution is made.

3. Staining: cell suspension is mixed with 0.4% trypan blue solution at 9:1. (final concentration 0.04%).

4. Counting: the living cells and dead cells are counted within three minutes respectively.

5. Observation under the microscope: the dead cells are dyed blue, while the living cells refuse staining and remain therefore transparent.

6. Statistic analysis on the viability of cells: living cell rate (%)=total number of living cells/(total number of living cells+total number of dead cells)*100%.

Figure 14:
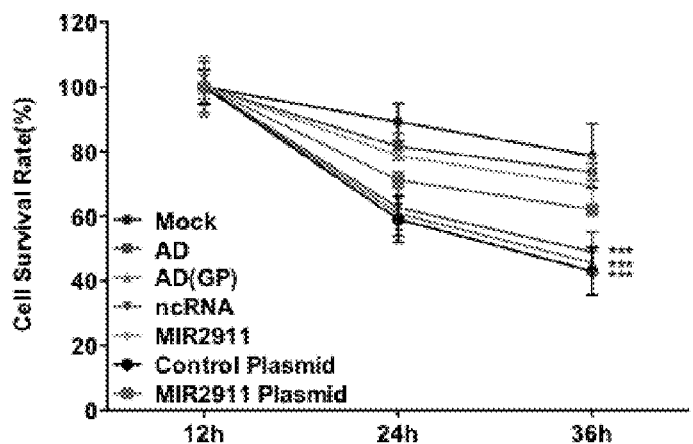
FIG. 14 shows the effect of GP on the survival rate of HUVEC cells using Trypan blue staining.

The results are shown as follows:

FIG. 14 shows the effect of GP on cell state of HUVEC cell using Trypan blue staining.

Mock: the cells with no treatment are negative controls; AD: adenovirus with empty plasmid; AD(GP): adenovirus that expresses eGFP coupled, Ebola encoding GP gene; ncRNA:transfection with random control nucleoacids after 12 h infection of adenovirus that expresses eGFP coupled, Ebola encoding GP gene; MIR2911: transfection with MIR2911 precursor mimics after 12 h infection of adenoviruses that express eGFP coupled, Ebola encoding GP gene; Control Plasmid: transfection with blank pcDNA6.2 plasmids after 12 h infection of adenoviruses that express eGFP coupled, Ebola encoding GP gene; MIR2911 Plasmid: transfection with MIR2911 over-expression pcDNA6.2 plasmids after 12 h infection of adenovirus that expresses eGFP coupled, Ebola encoding GP gene.

Being compared with the ncRNA and Control Plasmid group, the cell survival rate decreases significantly in the group transfected with MIR2911 and MIR2911 plasmids. GP protein can promote cell death, while MIR2911 and MIR2911 over-expression plasmids can inhibit the promotion of GP protein on cell death.

Figure 15:
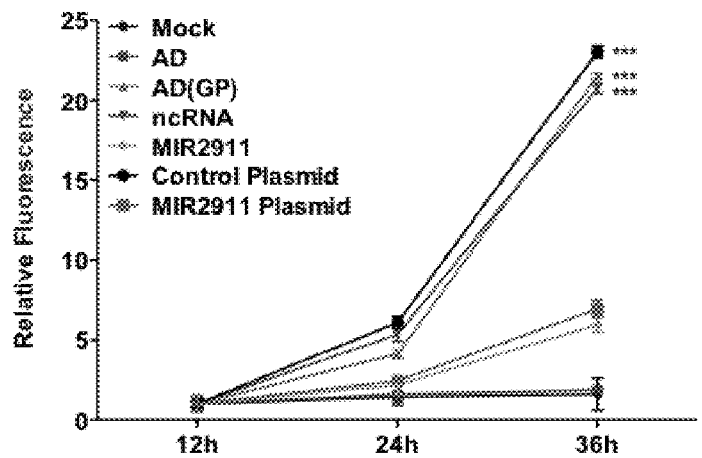
FIG. 15 shows the effect of GP protein on the integrity of endothelial cell membrane detected by cytotoxicity assay kit.

FIG. 15 shows the effect of GP protein on the integrity of endothelial cells membrane detected with the cytotoxicity assay kit. The significance of each legend is the same as in FIG. 14.

Being compared with ncRNA and the control plasmid group, the integrity of endothelial cells membrane is significantly improved in the group of MIR2911 and MIR2911 plasmid transfection. The results show that GP protein can destroy the integrity endothelial cell membrane, while MIR2911 and MIR2911 over-expression plasmids can inhibit the destruction of GP protein on endothelial cell.

Example 12. Validation of the Preventive Effect of Lonicera japonica Decoction on Ebola Virus, and the Therapeutic Effect of MIR2911 Expression Plasmids on Ebola Virus in Mice In Vivo Experimental method is shown as follows:

Control group one: Five mice with normal feeding and no treatment

Control group two: Five mice with normal feeding are treated since the third day with tail vein injection of adenovirus with empty plasmid (AD) at a dose of $10^8$ IU, for three consecutive days. The mice are then sacrificed on the eighth day.

Control group three: Five mice with normal feeding are treated since the third day with tail vein injection of adenovirus expressing GP gene [AD (GP)] at a dose of about $10^8$ IU for three consecutive days. The mice are sacrificed on the eighth day.

Experimental group one: Five mice, each drinks since the first day three milliliter of Lonicera japonica decoction per day, since the third day are treated with tail vein injection of adenovirus that expresses eGFP coupled, Ebola encoding GP gene (adenovirus expressing GP) at a dose of $10^8$ IU for three consecutive days. The mice are then sacrificed on the eighth day.

Experimental group two: Five mice, each drinks since the first day three milliliter of Lonicera japonica decoction per day, since the third day are treated with tail vein injection of adenovirus that expresses eGFP coupled, Ebola encoding GP gene at a dose of $10^8$ IU for three consecutive days; since the fifth day are injected via tail vein MIR2911 plasmids following the adenovirus injection at a dose of 5 mg/kg for 3 consecutive days. The mice are then sacrificed on the eighth day.

The mortality of each group is recorded, and the tissues and blood are collected to test the related biochemical indexes. The content of alanine aminotransferase (AST), aspartate aminotransferase (ALT) and total bilirubin (TB) in mice serum is detected using ELASA method. Being sacrificed, the mice are dissected and the changes of the liver and spleen are observed. And the expression level of TGFα, IL-6 in mice serum is detected using real-time PCR; HE staining of liver and spleen observed.

Figure 16:
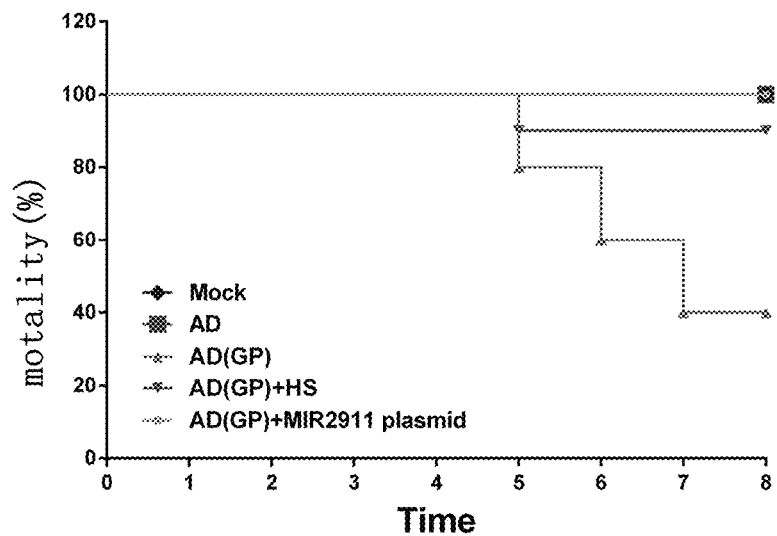
FIG. 16 shows the mice survival rate in the course of the experiments.

The results are shown as follows:

FIG. 16 shows the survival rate in the course of the experiment. Adenovirus with empty plasmid has no effect on the survival rate of mice, while adenovirus expressing GP gene injection is strongly lethal to the mice, the survival rate is 40%. When mice were administered Lonicera japonica decoction as a preventive treatment, the survival rate of mice is significantly elevated to 90%, while the mice treated with tail vein injection of MIR2911 over-expression plasmids are almost all cured. The results show that Lonicera japonica decoction can significantly prevent Ebola virus infection and significantly reduce the mortality rate, and MIR2911 plasmids can effectively treat Ebola virus.

Figure 17:
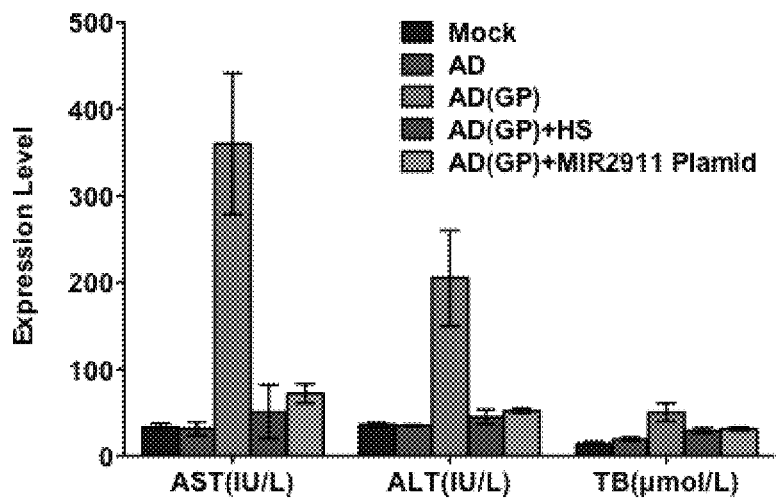
FIG. 17 shows the expression level of AST, ALT and TB.

FIG. 17 shows the expression level of AST, ALT and TB. Adenovirus expressing GP gene causes liver damage in mice and the expression level of AST, ALT and TB increase in the mice treated with tail vein injection of adenovirus expressing GP gene, while in the mice treated with MIR2911 over-expression plasmids or administered with Lonicera japonica decoction, the expression level of AST, ALT and TB are significantly decreased.

Meanwhile, observation in the mouse anatomy finds that the liver and spleens of mice infected with adenovirus expressing GP are significantly enlarged, while the enlargement are significantly alleviated after being treated with MIR2911 over-expression plasmids or Lonicera japonica decoction.

Figure 18:
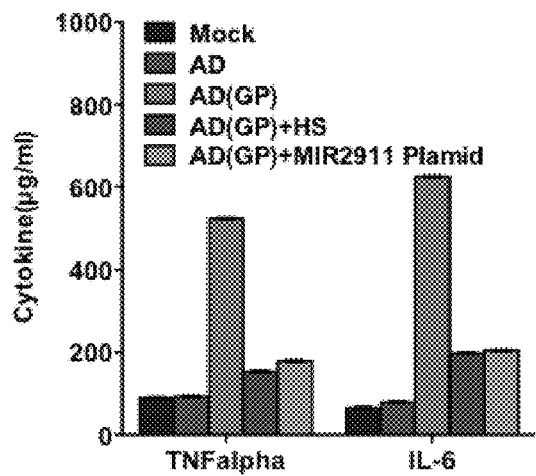
FIG. 18 shows the expression level of TGFα and IL-6 in serum.

FIG. 18 shows the expression level of TGFα and IL-6 in serum. The expression level of TGFα and IL-6 significantly increase in mice treated with tail vein injection of adenovirus expressing GP gene, while the mice treated with MIR2911 over-expression plasmids or Lonicera japonica decoction, the expression level of TGFα and IL-6 decrease significantly.

Figure 19:
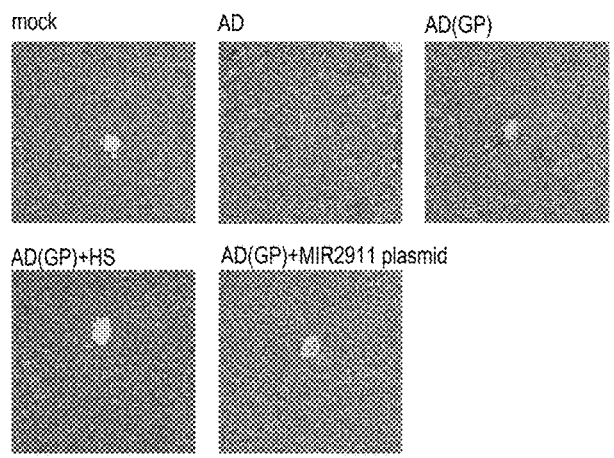
FIG. 19 shows the results of HE staining of liver.

FIG. 19 shows the results of HE staining of liver. After the injection of adenovirus with GP, obvious damage appears, but when being treated with MIR2911 expressing plasmid or Lonicera japonica decoction, the damage is significantly alleviated.

Figure 20:
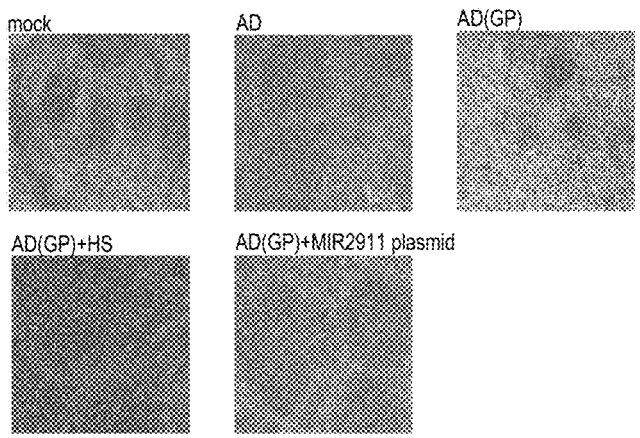
FIG. 20 shows the results of HE staining of spleen.

FIG. 20 shows the results of HE staining of spleen. After the injection of adenovirus with GP, obvious damage appears, but when being treated with MIR2911 expression plasmid or Lonicera japonica decoction, the damage is significantly alleviated.

To sum up, MIR2911 expression plasmid or Lonicera japonica decoction has a significant inhibiting effect on adenovirus with GP, Lonicera japonica decoction has preventive effect on Ebola virus, and MIR2911 expression plasmid has therapeutic effect on Ebola virus.

All documents referred to in the present invention are incorporated by reference as if each reference is cited alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A method for inhibiting expression of a protein of an Ebola virus comprising: administering MIR-2911 or an extract or a composition containing MIR-2911 to a subject in need thereof,
   wherein the protein of the Ebola virus is GP, or VP40, or a combination thereof,
   the subject is infected with the Ebola virus, and
   the MIR-2911 or the extract or the composition inhibits expression of GP and VP40 of the Ebola virus in the subject.

2. The method of claim 1, wherein the composition comprises: (a) a pharmaceutical acceptable carrier; and (b) an active ingredient comprising MIR-2911, and
   the active ingredient accounts for 0.1-90 wt % of the total weight of the composition.

3. The method of claim 1, wherein the subject is human.

4. The method of claim 1, wherein the MIR-2911 comprises artificially synthesized MIR-2911, plant MIR-2911, MIR-2911 precursor, MIR-2911 mature form, and/or a plant or a plant part containing MIR-2911.

5. The method of claim 1, wherein the Ebola virus is selected from the group consisting of: Bundibugyo ebolavirus (BDBV), Zaire ebolavirus (EBOV), and Sudan ebolavirus (SUDV).

6. A method for inhibiting destruction or death of endothelial cells caused by GP of Ebola virus, wherein the method comprises the following step: administering MIR2911 or an extract or a composition containing MIR2911 to a subject in need thereof.

7. A method for inhibiting Ebola virus, wherein the method comprises the step of contacting miR2911 with Ebola virus or cells infected with Ebola virus.

8. The method of claim 7, wherein the Ebola virus is selected form the group consisting of: Bundibugyo ebolavirus (BDBV), Zaire ebolavirus (EBOV) and Sudan ebolavirus (SUDV).

* * * * *